United States Patent [19]

Baba et al.

[11] Patent Number: 5,679,950

[45] Date of Patent: Oct. 21, 1997

[54] ION TRAPPING MASS SPECTROMETRY METHOD AND APPARATUS THEREFOR

[75] Inventors: Takashi Baba, Hatoyama-machi; Izumi Waki, Asaka, both of Japan

[73] Assignee: Hitachi, Ltd., Tokyo, Japan

[21] Appl. No.: 626,560

[22] Filed: Apr. 2, 1996

[30] Foreign Application Priority Data

Apr. 3, 1995 [JP] Japan .................... 7-077517

[51] Int. Cl.⁶ .................................................. H01J 49/42
[52] U.S. Cl. ...................... 250/281; 250/282; 250/292
[58] Field of Search ............................... 250/281, 282, 250/288, 290, 291, 292, 293

[56] References Cited

U.S. PATENT DOCUMENTS

| 2,939,952 | 6/1960 | Paul et al. ............... | 250/41.9 |
|---|---|---|---|
| 4,540,884 | 9/1985 | Stafford et al. ........... | 250/282 |
| 4,736,101 | 4/1988 | Syka et al. ............... | 250/292 |
| 4,755,670 | 7/1988 | Syka et al. ............... | 250/292 |
| 5,134,286 | 7/1992 | Kelley ..................... | 250/282 |
| 5,248,883 | 9/1993 | Brewer et al. ............. | 250/281 |

OTHER PUBLICATIONS

Physical Review A, vol. 21, No. 5, May 1980, pp. 1606–1617; J.P. Gordon et al.: *Motion of atoms in a radiation trap.*
Physical Review Letters, vol. 59, No. 26, 28 Dec. 1987, pp. 2931–2934; F. Diedrich et al.: *Observation of a Phase Transition of Stored Laser–Cooled Ions.*
Physical Review Letters, vol. 57, No. 1, 7 Jul. 1986, pp. 70–73; D.J. Larson et al.: *Sympathetic Cooling of Trapped Ions: A Laser–Cooled Two–Species Nonneutral Ion Plasma.*
Physical Review Letters, vol. 60, No. 20, 16 May 1988, pp. 2022–2025; S.L. Gilbert et al.: *Shell–Structure Phase of Magneticallyu Confined Strongly Coupled Plasmas.*
Optics Letters, vol. 18, No. 9, 1 May 1993, pp. 732–734; G.P. Barwood et al.: *Observation of the $5s^2S_{1/2}-4d_2D_{5/2}$ transition in a single laser–cooled trapped $Sr^+$ ion by using an all–solid–state system of lasers.*
Applied Physics, vol. 17, 1978, pp. 123–129; W. Neuhauser et al.: *Visual Observation and Optical Cooling of Electrodynamically Contained Ions.*
Physical Review A, vol. 45, No. 9, 1 May 1992, pp. 6493–6501; M.G. Raizen et al.: *Ionic crystals in a linear Paul trap.*
Physical Review A, vol. 44, No. 1, 1 Jul. 1991, pp. R20–R23; A.S. Bell et al.: *Laser cooling of trapped ytterbium ions using a four–level optical–excitation scheme.*
The Quantum Physics of Atomic Frequency Standards, vol. 2, Adamn Hilger, 1989, pp. 1498–1502; J. Vanier et al.
IEEE Transactions on Instrumentation and Measurement, vol. 38, No. 2, Apr. 1989, pp. 524–532; Jürgen Helmcke et al.: *Optical Frequency Standards.*
Physical Review Letters, vol. 68, No. 13, 30 Mar. 1992, pp. 2007–2010; I. Waki eta l.: *Observation of Ordered Structures of Laser–Cooled Ions in a Quadrupole Storage Ring.*

*Primary Examiner*—Kiet T. Nguyen
*Attorney, Agent, or Firm*—Kenyon & Kenyon

[57] ABSTRACT

An ion trapping mass spectrometer permitting highly sensitive mass spectrometry through in-situ observation. The mass spectrometer comprises ion trapping electrodes, a laser device for generating a cooling laser beam and a photo detector. The ion trapping electrodes generate a field in which to store sample ions and laser-cooled probe ions concurrently. The ions are cooled by laser as well as by the effect of sympathetic cooperative cooling, whereby intense resonance scattering light is acquired from the probe ions. An analyzing AC electric field is applied to the sample ions while the field is being scanned in frequency. Resulting changes in the resonance scattering light and spatial distribution of the probe ions are observed for mass spectrometry.

24 Claims, 14 Drawing Sheets

FIG. 1 *PRIOR ART*
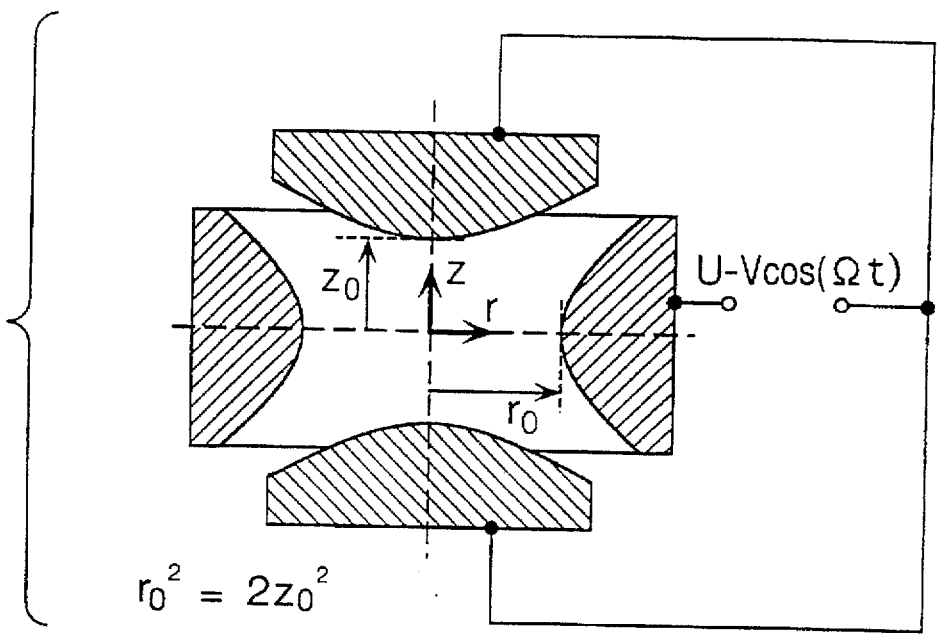
$r_0^2 = 2z_0^2$
FIG. 2 *PRIOR ART*
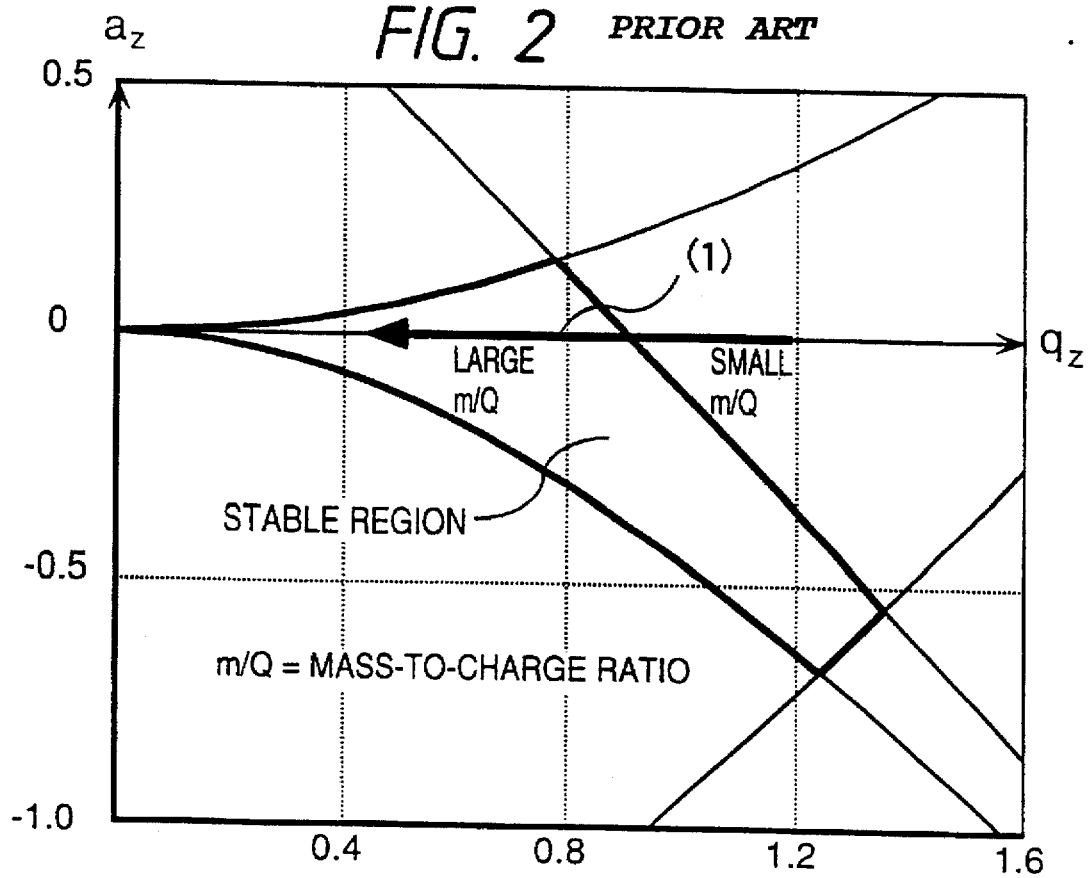
m/Q = MASS-TO-CHARGE RATIO

ION TRAPPING MASS SPECTROMETRY METHOD AND APPARATUS THEREFOR

BACKGROUND OF THE INVENTION

The present invention relates to an ion trapping mass spectrometry method offering higher sensitivity than before and an apparatus therefor.

In the fields of environmental technology and semiconductor fabrication, growing needs have been recognized in recent years for trace chemical analysis of organic material. Instrumentation for such detection must analyze numerous samples. Given that requirement, analyzing equipment needs to be inexpensive and easy to use beside offering high levels of sensitivity. Traditionally, quadrupole ion trapping mass spectrometry has been used extensively as the basis for such analyzers that meet above requirements. The reason for this method to be preferred is threefold: analyzing equipment operating on this method is made small in size and simply structured; the range of analyzable masses is sufficiently extensive (1 to 1,000) to deal effectively with mass spectrometry of organic molecules; and the equipment operating on this method stores ions before their analysis and thus is more sensitive than radio frequency quadrupole mass filters.

An overall, in-depth description of the related art regarding quadrupole ion trapping mass spectrometry is found in "Quadrupole Storage Mass Spectrometry" by R. E. March and R. J. Hughes (John Wiley & Sons, 1989; cited hereunder as reference 1).

The typical method of ion trapping spectrometry involves three kinds of key components: ion sources for generating ions, a radio frequency quadrupole electrode arrangement for storing ions, and ion detecting means for subjecting the sample ions to mass spectrometry for detection.

A variety of ion sources are being developed in accordance with different purposes of analysis. The simplest way of ionization is that of radiating an ionizing electron beam onto the sample injected into the storage region of the trapping electrodes. In the field of environmental technology today, atmospheric pressure ionization or chemical ionization combined with gas chromatography or liquid chromatography is also used to separate target samples. In the field of semiconductor fabrication, laser surface desorption and laser ionization are utilized to analyze surface contamination of silicon wafers.

The radio frequency quadrupole electrode arrangement for storing ions (i.e., ion trapping electrodes) involves the use of the so-called Paul trap. The trap captures ions in a three-dimensional radio frequency quadrupole electric field such as one shown in FIG. 1. The principles of operation for the Paul trap to capture ions are described in the above-cited reference 1. There are two specific parameters, a and q, for describing the stability of ions in the ion trap. The two parameters in r and z directions are defined by the following equations (1) and (2): r direction;

$$a_r = 4QU/(m\Omega^2 r_0^2) \quad \} \quad (1)$$
$$q_r = 2QV/(m\Omega^2 r_0^2) \quad \}$$

z direction;

$$a_z = -2a_r \quad \} \quad (2)$$
$$q_z = -2q_r \quad \}$$

where, m stands for the mass of ions, Q for their electric charge, V for the amplitude of the radio frequency electric field, D for its frequency, U for the DC voltage value, and $2r_0$ for the inner diameter of the ring electrode. Using the above two parameters provides a region of stability, shown enclosed in thick lines in FIG. 2, which determines the conditions under which ions are trapped.

The ion detecting means in the early days of ion trapping mass spectrometry was that of measuring the vibration of ions which is dependent on their mass (U.S. Pat. No. 2,939,952). Inside the ion trap of this setup, ions are trapped by a harmonic mean potential (called pseudo-potential) stemming from the radio frequency quadrupole electric field. The trapped ions oscillate harmonically in the presence of the pseudo-potential. This harmonic oscillation is called secular motion. When the DC voltage is zero, i.e., where $a_r = a_z = 0$ and $q_z \leq 0.4$, the secular frequency is proportional to the mass-to-charge ratio through the parameter q. That is, the frequency is given by the equations:

$$\omega_r = \Omega q_r/2 \sqrt{2} \quad (3)$$

$$\omega_z = \Omega q_z/2 \sqrt{2} = 2\omega_r \quad (4)$$

where, $\omega_r$ denotes the secular frequency in the r direction and $\omega_z$ represents the same in the z direction. Even when a ≠0 or $q_z > 0.4$, $\omega_r$ and $\omega_z$ are given as a known function of a and q (see reference 1). Thus mass spectrometry of sample ions is always made possible by knowing the secular frequencies of the ions to be analyzed.

The detecting means of ion trapping mass spectrometry in its early days involved detecting a current induced in the ion trapping electrodes by the ions oscillating inside these electrodes. This method has had difficulty in achieving high sensitivity because of the need to detect a very small current. With this method in use, the minimum number of ions that may be detected is about 1,000.

Today's preferred widespread method of ion trapping mass spectrometry is the method of mass selective instability mode operation invented in 1985 (U.S. Pat. No. 4,540,884). With this method in use and with the DC voltage being zero, ions of different masses line up on the q axis indicated in FIG. 2. Then ions meeting the relation of $q_z < 0.908$ are trapped within the ion trap. That is, ions that meet the requirement of $$m > 2QU/(0.908\Omega^2 r_0^2) \quad (5)$$

are trapped by the ion trap.

The method of mass selective instability mode operation works as follows: first, the amplitude U of the radio frequency electric field is set to a small value. Ions are then stored under the condition of a radio frequency amplitude that guarantees the stability of many kinds of ions. Thereafter, the radio frequency amplitude U of the electric field trapping the ions is scanned from the low to the high amplitude. The scanning operation destabilizes the stored ions within the ion trap starting from the lightest ions. When thus destabilized, the ions escape, light ones first followed by heavier ones, from the ion trapping electrodes in the direction of the z axis. The number of the escaping ions are measured synchronously with the scanning of the radio frequency amplitude. This makes it possible to know the kinds of ions and their masses trapped inside the ion trap. When it was introduced, the method expanded the range of masses that may be analyzed, enhanced the resolution of analyses, and improved the ease of operation. Ion trapping mass spectrometers became practical.

In 1988 came the invention of the method of mass selective instability mode operation involving resonant ejection, as disclosed in Japanese Patent Laid-Open No. Hei 5-121042 (corresponding to U.S. Pat. No. 4,736,101). The disclosed invention involves applying a supplemental AC frequency voltage resonating with the secular oscillation to the ion trapping electrode arrangement in addition to the ion trapping radio frequency electric field. When the ion trapping radio frequency electric field is scanned in its amplitude, the trapped ions inside are resonated continuously in the order of their mass-to-charge ratios. The escaping ions prompted by resonance are detected and their mass spectrum is obtained. The invention has proved effective in studying chemical reactions of molecular ions as well as in determining molecular structures. Independent of their ion trapping radio frequency electric field, the ion trapping electrodes are subjected to the supplemental AC frequency electric field. The supplemental AC frequency electric field causes molecular ions to oscillate and collide with ambient neutral gas ions. The collision destroys the molecular ions and produces daughter ions. The daughter ions are in turn subjected to mass spectrometry using the method of mass selective instability mode operation. The result is a spectrum that shows the structure of the parent molecular ions. The process is also called MS-MS mode or tandem mass spectrometry. In case the tandem process is repeated n times, it is called an n-iteration tandem mass spectrometry or $(MS/MS)^n$ method. With this method implemented, ion trapping mass spectrometry has become an important means for studying ion-molecule reactions as well as for determining molecular structures.

Then came the invention of a method that boosted the sensitivity of analysis by keeping sample ions trapped while selectively eliminating background ions during sample ion storage (U.S. Pat. No. 5,134,286). This invention works roughly as follows: while ions are being stored, the ion trapping electrode arrangement is supplied with a supplemental AC electric field having the same oscillation frequency as that of the secular motion of background ions. This resonates the background ions which are then ejected from the ion trapping electrode arrangement.

The conventional ion trapping mass spectrometer discussed in the reference 1 cited earlier is sensitive enough to detect a minimum of about 100 ions. This level of sensitivity is determined by two constraints: the amount of ions lost when ions are ejected from the ion trapping electrodes, and the signal-to-noise ratio of the ion detector currently in use. Under the constraints, little further improvement in terms of sensitivity is expected from the cited conventional method.

Detection of ions based on the method of mass selective instability mode operation involving resonance-induced ejection is a process of destructive (out-of-trap) measurement causing the loss of sample ions to be ejected from the ion trap. This means that once the mass spectrum of sample ions is acquired, the ions inside the analyzer disappear. As a result, no mass spectrum is obtained of intermediate products by use of the MS-MS mode or n-iteration tandem mass spectrometry method. If it is desired to obtain the spectrum of daughter ions at each of up to n stages, it is necessary to introduce sample ions n times. This requires preparing large quantities of sample ions, a major reason for prolonging the analyzing time involved and requiring a large amount of the sample.

SUMMARY OF THE INVENTION

It is therefore a general object of the present invention to provide an ion trapping mass spectrometry method and an apparatus for use therewith, whereby mass spectra are obtained of ultra trace amount of samples quickly and accurately.

It is a more specific object of the present invention to provide an ion trapping mass spectrometry method and an apparatus for use therewith, the apparatus being so sensitive that less than 100 sample ions, or even a single ion, may be detected in an in-situ (or in-trap) manner.

It is another object of the present invention to provide an ion trapping mass spectrometry method and an apparatus for use therewith, whereby MS-MS mode or n-iteration tandem mass spectrometry is performed to identify ion types at each of repeated stages in-situ inside the trap in the course of mass spectrometry.

The above objects may be achieved primarily according to one aspect of the invention, which provides optical means for detecting ions. An AC electric field is applied to sample ions for analysis, and the electric field is scanned in terms of frequency. The scanning causes the sample ions to oscillate by resonance at their secular frequency, which is detected by optical means. The principles involved are illustrated in FIG. 3. More about the setup of FIG. 3 will now be discussed.

The sample ions in the ion trap are supplemented by a specific species of ions which are trapped concurrently therein. It is assumed that the mass-to-charge ratio of the added ions is known, and that the added ions generate fluorescence of high intensity. Such fluorescent ions are called probe ions hereunder. In FIG. 3, the small filled circle denotes a sample ion and small hollow circles represent probe ions. A light beam is introduced into the sample to excite the probe ions optically, wherewith the motion of the probe ions is observed. The supplemental AC electric field $A\cos\omega t$ for analysis is then applied to the ion trap while being scanned in terms of its amplitude. When the secular frequency of the sample ions coincide with the frequency of the AC electric field, the sample ions oscillate by resonance. At this point, the sample ions are in Coulomb collision with the probe ions, disturbing the motion of the probe ions. Changes in the motion of the fluorescent probe ions are then detected optically. This provides an observable means of how the sample ions oscillate by resonance. How much the probe ions are influenced in a resonant oscillation by the sample ions depends on the quantity of the sample ions present. This means that the quantity of the sample ions may be measured by detecting the quantity of changes in the motion of the probe ions. In one of its variations, the present invention may be so implemented as to see whether a specific kind of ions is present. Such implementation need only furnish an AC electric field having a frequency at which the target ions oscillate by resonance. The above principles of operation, on which the present invention is based, constitute an analyzing scheme called fluorescent mass spectrometry hereunder.

These and other objects, features and advantages of the invention will become more apparent upon a reading of the following description and appended drawings.

BRIEF DESCRIPTION OF THE DRAWINGS

FIG. 1 is a schematic view of an electrode structure of a Paul trap;

FIG. 2 is a graphic representation showing a region of stability in the Paul trap of FIG. 1 and a mass spectrometry operation mode in connection therewith;

FIG. 7-1 is a schematic view illustrating the principles of an even further method of mass spectrometry according to the invention;

FIG. 7-2 is a schematic view showing the principles of a still further method of mass spectrometry according to the invention;

DESCRIPTION OF THE PREFERRED EMBODIMENTS

Where this invention is practiced, it is effective to adjust the number of probe ions in keeping with the number of sample ions. This is because too few probe ions hamper the provision of a sufficient quantity of light and result in an insufficient level of sensitivity, and because too many probe ions cannot be oscillated sufficiently by the sample ions. Obviously, the quantity of sample ions is generally unknown. It is thus practical to add sample ions gradually as spectrometry progresses until an optimum signal is obtained.

The amplitude of the supplemental AC electric field applied to the ion trap should be wide enough to permit an optical observation of changes in the motion of the probe ions when the sample ions oscillate by resonance. An excessively large amplitude of the AC electric field causes the sample ions to be ejected from the ion trapping electrodes; the amplitude must be smaller than that of a maximum voltage that would keep the sample ions from getting ejected from the ion trapping electrodes.

The analyzing operation tends to increase the kinetic energy of sample and probe ions. Before the continuous increase in the kinetic energy of trapped ions eventually causes the ions to be ejected from the ion trap, that kinetic energy needs to be dissipated. This requires furnishing a cooling process for depriving the trapped ions of their kinetic energy. One way to implement the cooling process is by placing the ion trapping electrode arrangement in a thin helium gas atmosphere of 100 Pa or less. In such an atmosphere, the sample and probe ions collide with helium gas atoms and lose their kinetic energy during the process. Another way to implement the cooling process involves an application of laser cooling. In this case, photo-excitation for measuring purposes may be used as a means for cooling, as well as will be described later in more detail in connection with an embodiment of the invention. In specific terms, changes in the motion of probe ions mean an increase in their average velocity. This is because the probe ions receive kinetic energy from the sample ions as a result of Coulomb collision. With their average velocity boosted, the probe ions expand in their spatial distribution.

In measuring changes in the motion of probe ions, the present invention contemplates the use of one of five methods described below.

Figure 3:
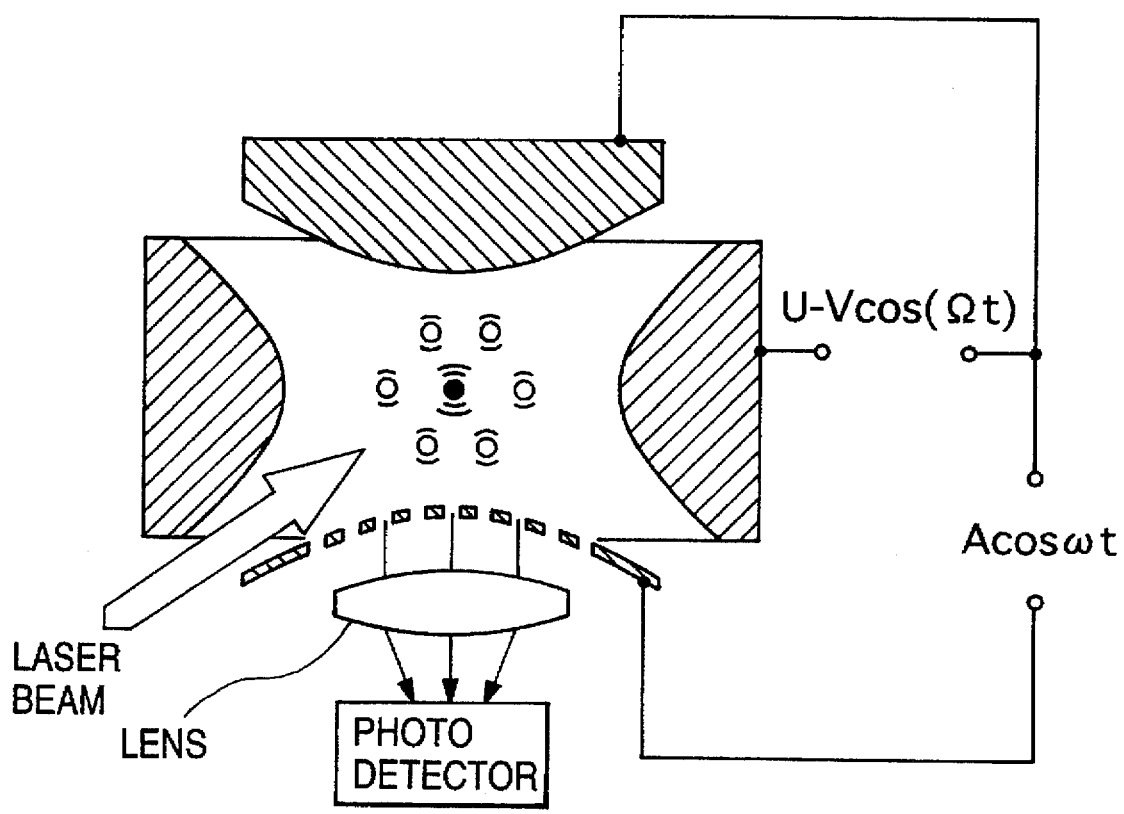
FIG. 3 is a schematic view illustrating the general principles of the present invention when applied to a Paul trap.
Figure 4:
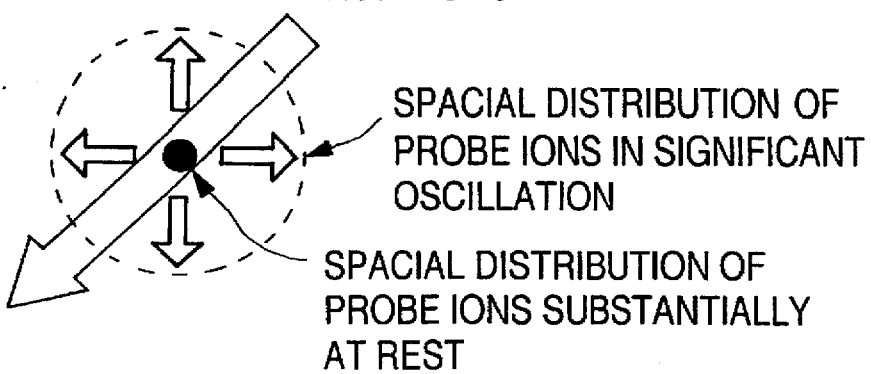
FIG. 4 is a schematic view depicting the principles of one method of mass spectrometry according to the invention.
Figure 18:
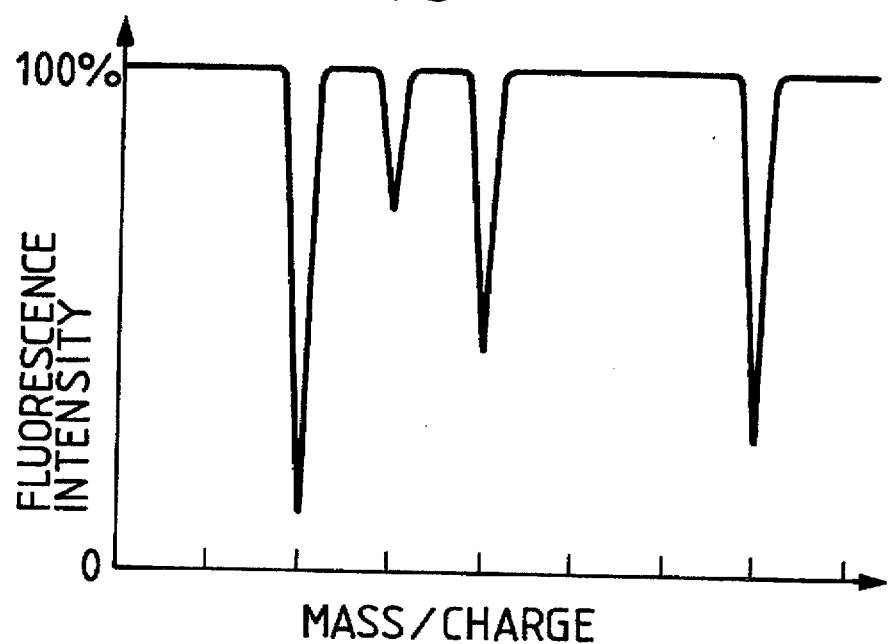
FIG. 18 is a graphic representation indicating a typical mass spectrum acquired by the invention.

The first method of fluorescent mass spectrometry, as shown in FIG. 4, involves introducing a finely focused laser beam into the center of the ion trapping electrode arrangement. With probe ions as a whole expanded in their spatial distribution, the number of the probe ions within the laser beam decreases. According to this method, the intensity of fluorescence is measured to be lower when sample ions oscillate by resonance than when the sample ions do not resonate. The number of the sample ions is derived from the decrease in the intensity of fluorescence. Where the changes involved are a small fraction of the total fluorescence, there exists a linear relationship between the decrease in the intensity of fluorescence and the number of sample ions. In this case, a mass spectrum such as one shown in FIG. 18 is observed.

Figure 5:
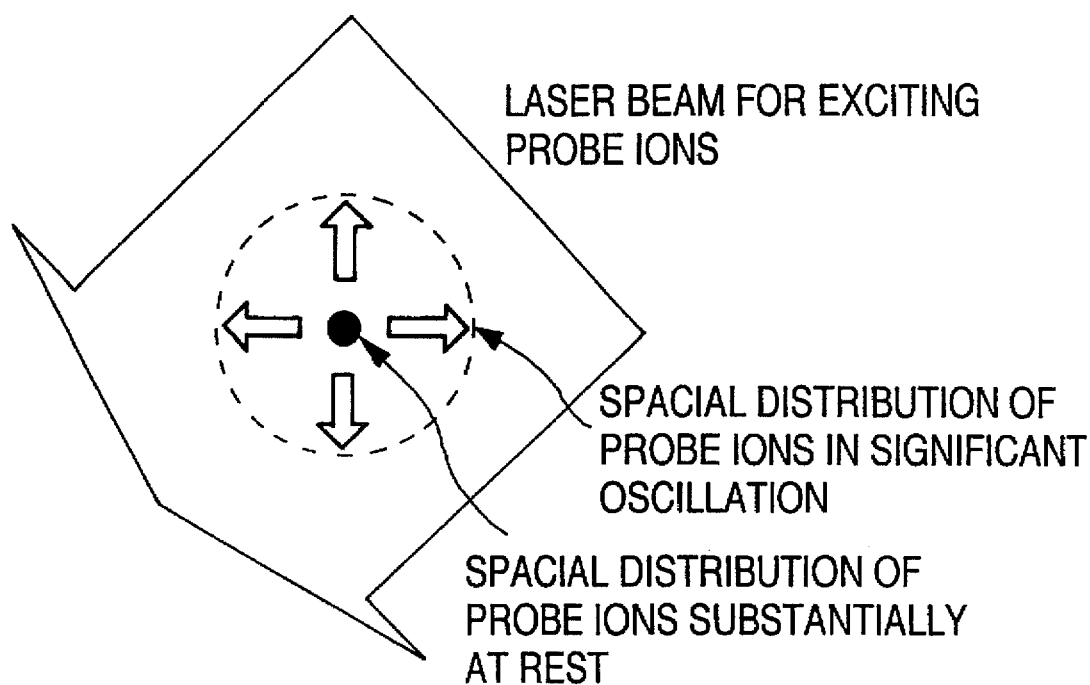
FIG. 5 is a schematic view depicting the principles of another method of mass spectrometry according to the invention.
Figure 19:
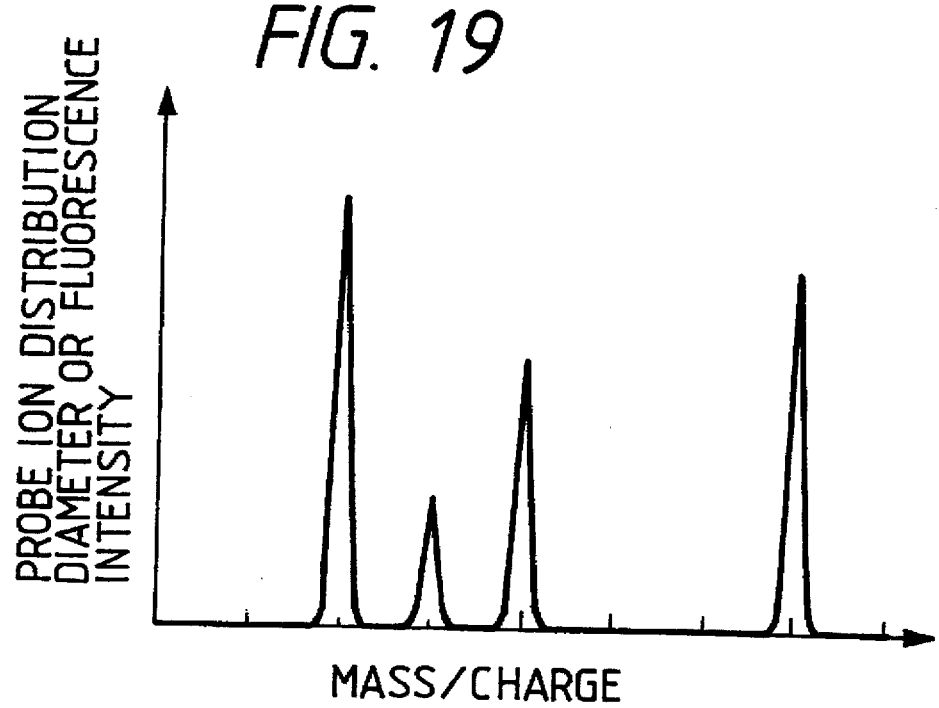
FIG. 19 is a graphic representation showing another typical mass spectrum obtained by the invention.

The second method of fluorescent mass spectrometry, as shown in FIG. 5, involves radiating light broadly and uniformly inside the ion trapping electrodes. With the probe ions expanded in their spatial distribution, the fluorescent spread in space increases. That is, the spatial distribution of fluorescence is measured to be more broadly spread when the sample ions oscillate by resonance than when they do not resonate. The amount of expansion of fluorescence reveals the number of sample ions. In this case, a mass spectrum such as one illustrated in FIG. 19 is observed.

Figure 6:
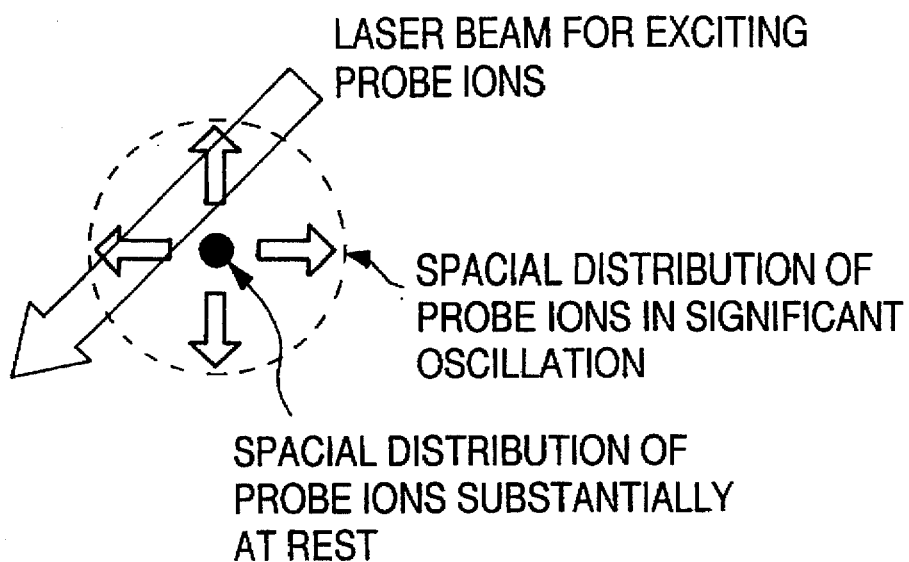
FIG. 6 is a schematic view indicating the principles of a further method of mass spectrometry according to the invention.

The third method of fluorescent mass spectrometry, as shown in FIG. 6, involves introducing a finely focused laser beam off the center of the ion trapping electrodes. With the probe ions as a whole expanded in their spatial distribution, the number of probe ions inside the laser beam increases. That is, the intensity of fluorescence is measured to be higher when the sample ions oscillate by resonance than when the sample ions do not resonate. The amount of increase in the intensity of fluorescence reveals the number of the existing sample ions. Where the changes involved are a small fraction of the maximum (or saturated) fluorescence, there exists a linear relationship between the increase in fluorescence intensity and the number of sample ions. In this case, a mass spectrum such as one shown in FIG. 19 is observed.

Figures 1, 7:
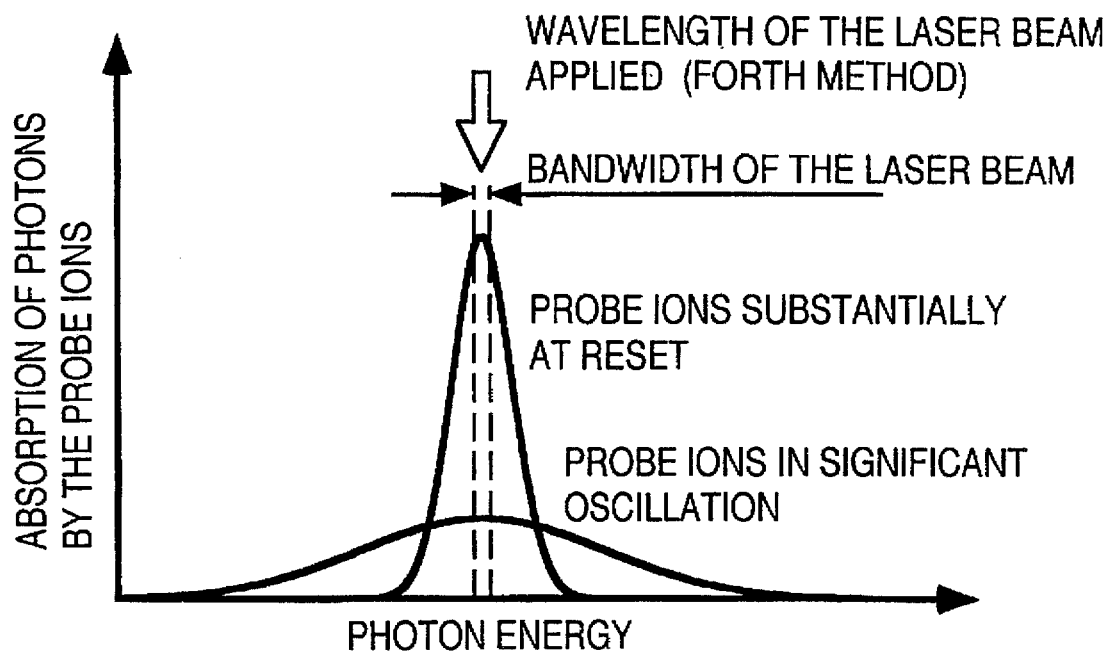

The fourth method of fluorescent mass spectrometry involves the use of probe ions whose absorption spectral bandwidth is especially narrow. In this case, a velocity increase in the motion of probe ions broadens their absorption spectral bandwidth through the Doppler effect, as shown in FIG. 7-1. If the wavelength of a single mode laser beam is set close to the center wavelength of the absorption spectrum of the probe ions, then an increase in the velocity of the probe ion motion lowers the probability of light absorption. That is, the intensity of fluorescence is measured to be lower when the sample ions oscillate by resonance than when the sample ions do not resonate. The amount of the decrease in fluorescence intensity reveals the number of the existing sample ions. Where the changes involved are a small fraction of the total fluorescence, there exists a linear relationship between the decrease in fluorescence intensity and the number of sample ions. In this case, a mass spectrum such as one shown in FIG. 18 is observed.

As with the fourth method, the fifth method of fluorescent mass spectrometry involves the use of probe ions whose absorption spectral bandwidth is especially narrow. Like the fourth method, the fifth method utilizes a single mode laser beam which is introduced with its wavelength shifted off the center wavelength of the absorption spectrum of the probe ions (see FIG. 7-2). In this case, the coefficient of optical absorption will increase when the velocity distribution of the probe ions is broadened. In this setup, the intensity of fluorescence is measured to be higher when the sample ions oscillate by resonance than when the sample ions do not resonate. The amount of the increase in fluorescence reveals the number of the existing sample ions. In this case, a mass spectrum such as one shown in FIG. 19 is observed.

According to any one of the above-described five methods, there exists a functional relation between two factors: the amount of changes in fluorescence intensity or spatial distribution resulting from changes in the probe ion motion on the one hand, and the number of sample ions on the other. In particular, in a region where oscillating changes involved are small, there exists a linear relationship between the amount of changes in fluorescence intensity and the number of sample ions. Thus the AC electric field for causing the target sample ions to oscillate for analysis should preferably have the smallest possible amplitude that would still permit detection of changes in fluorescence intensity at a sufficiently high level of sensitivity.

Where the Paul trap such as one on FIG. 1 is used, the secular frequency in the z direction differs from that in the r direction. However, there exists the relation:

$$\omega_z = 2\omega_r$$

Thus with the frequency $\omega_r$ appearing in addition to the frequency $\omega_z$. The two frequencies may still be separated by a software means using the relation between the two secular frequencies. If a linear ion trap (to be described later) is used, then there will be the relation:

$$\omega_z = \omega_r$$

The problem above does not appear.

How to improve the sensitivity of fluorescent mass spectrometry based on the above principles will now be described. One way to boost the sensitivity of fluorescent mass spectrometry is by enhancing the efficiency in detecting fluorescence intensity, i.e., the efficiency of collection the fluorescence optically. Specifically, an optical waveguide may be installed close to the ion trapping electrode arrangement. In operation, light is guided through the optical waveguide to a photo detector for better efficiency of light collection. Drawing on the same principle, another setup for higher optical collection efficiency may be one in which the ion trapping electrodes are made up of thin metal plates or metal meshes with one or more of through holes thereon. A objective lens or mirror is provided close to such through holes. The fluorescence collected by the lens or mirror is guided by way of the holes to the photo detector for better efficiency of optical detection.

Another way to boost the sensitivity of fluorescent mass spectrometry involves the use of means for eliminating adverse effects of unnecessary light such as stray light. Specifically, the AC electric field for oscillating sample ions by resonance for analysis is modulated in amplitude. In this setup, changes in fluorescence intensity or in spatial distribution are measured synchronously with the modulation frequency in use. The modulation frequency here should preferably be smaller than the secular frequency of sample or probe ions and small enough not to affect adversely the resolution of mass spectrometry. Synchronous measurement may be implemented through lock-in detection procedures.

There are two components making up the oscillation frequency for probe ions that are in Coulomb collision with the resonant sample ions. One oscillation frequency component is the secular frequency of the probe ions in use. As the kinetic energy of the probe ions increases, there develops modulation synchronous with the secular motion, i.e., basic oscillation, of the probe ions. The other oscillation frequency component for the probe ions is the secular frequency for sample ions to be analyzed. That is, when sample ions collide with probe ions periodically, the probe ions come to possess the secular frequency of the sample ions.

Figures 2, 7:
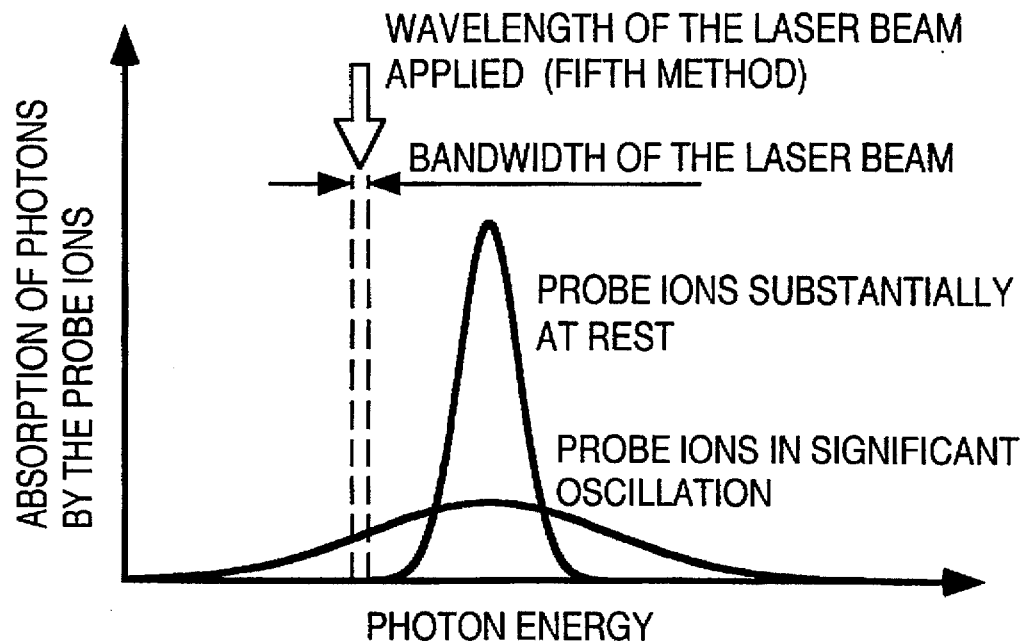

In operation of the lock-in detection of the fluorescence, the laser beam is introduced at an angle of incidence such that the direction of the laser beam has a geometrical component in parallel with the oscillation of the probe ions, whereby one of the two oscillation frequency components is captured. More specifically, the incident laser beam is arranged to have an angle of 85 degrees or less preferably parallel with respect to the AC electric field for oscillating ions for analysis. Preferably, the linewidth of the laser frequency is narrow as depicted in FIG. 7-1 or FIG. 7-2. In the setup in which the laser beam is introduced into the ion trap as described, the probability of probe ions absorbing and scattering incident light differs between the following two cases due to the Doppler effect: one in which such probe ions have a kinetic component parallel to the laser beam, and the other in which the probe ions have a kinetic component anti-parallel to the laser beam. That is, the intensity of fluorescence emitted by the probe ions is modulated by their oscillation frequency due to Doppler effect. It follows that if fluorescence intensity is measured synchronously with the secular frequency of probe ions, with the frequency of the AC electric field for analysis, or with the sum or difference between the two frequencies, then the process is equivalent to directly observing the oscillating state of the probe ions. That in turn eliminates the adverse effects of stray light, enhancing the sensitivity of mass spectrometry.

Furthermore, where probe ions with a narrow absorption spectrum are utilized, the spatial position of incidence of the applied laser beam, as depicted in FIG. 4 or FIG. 5, and its wavelength, as depicted in FIG. 7-1 or FIG. 7-2, may be combined optimally so as to enhance signal intensity, as shall be described below.

For signals such as that of FIG. 18 whose intensity falls at resonance as indicated, the above-described first and fourth methods of fluorescent mass spectrometry are combined for optimal signal. Specifically, the wavelength of the applied laser beam is set close to the center wavelength of the absorption spectrum of the probe ions in use. The laser beam is finely focused before being introduced into the center of the ion trap for fluorescent mass spectrometry.

Because the first and the fourth methods are both intended to obtain signals whose fluorescence intensity decreases, the two methods when combined prove to be more efficient than ever in providing a signal of high intensity than when applied independently.

Conversely, for signals such as that of FIG. 19 whose intensity increases as shown, the above-described third and fifth methods of fluorescent mass spectrometry are combined. Specifically, the wavelength of the applied laser beam is shifted off the center frequency of the absorption spectrum of the probe ions in use, as illustrated in FIG. 7-2. The laser beam is finely focused before being introduced into the ion trap off its center for fluorescent mass spectrometry. Because the third and the fifth methods are both intended to obtain signals whose fluorescence intensity increases at resonance, the two methods when combined also prove to be more efficient than ever in providing a signal of high intensity than applying independently.

Yet another way to enhance the sensitivity of detection involves the use of a laser-cooled type of ions as probe ions in a laser cooling setup. When laser-cooled ions are subjected to the radiation of a laser beam that resonates with their excitation level, the ions are excited to emit fluorescence. If the wavelength of the applied laser beam is slightly longer than the center wavelength of resonance, the probe ions are deprived of their kinetic energy and cool down. The laser cooling scheme based on this principle is called the Doppler cooling method offering the highest cooling efficiency yet. The theory supporting this method is described illustratively by J. P. Gordon and A. Ashkin in Physical Review, Vol. A21, p. 1606 (1980; called reference 2 hereunder).

The laser cooling scheme permits higher levels of detection sensitivity for the following reasons: first of all, laser-cooled ions are deprived of their kinetic energy. Without laser cooling, the ion temperature is 300K or higher. The absorption spectrum is substantially broadened by the Doppler effect. With laser-cooling, the ion temperature can be lowered to about mK very efficiently. The laser cooling causes the absorption spectral line to narrow substantially from its pre-cooling broadened state (due to the Doppler effect) down approximately to its natural width. The cooled ions emit fluorescence intense enough to allow even a single ion to be observed (F. Diedrich et at., Physical Review Letters Vol. 59, p. 2931 (1987; called reference 3 hereunder) ). The sufficiently cooled ions repulse one another by the Coulomb force and form into a state of regularly arranged ions, the so-called Wigner crystal state (reference 3). If laser-cooled ions and ions not cooled by laser are both trapped in the same ion trap, those ions which would not be cooled by the laser are also cooled because they are coupled to the laser-cooled ions by the Coulomb force (D. J. Larson et al., Physical Review Letters 57 70 (1986), p. 55 (1990); called reference 4 hereunder). This phenomenon is called sympathetic cooling. It should be noted that there exist only limited types of ions to which laser cooling may be applied. The most typical of these ions are singly charged positive ions of alkaline earth metals. Table 1 below lists typical isotope ions that may be cooled by laser in a relatively simple manner.

TABLE 1

Typical Laser-Cooled Ions

| Ion Type | Laser Beam Wavelength Needed for Laser Cooling (nm) | References |
|---|---|---|
| $^9Be^+$ | 313 | S. L. Gilbert et al.; Physical Review Letters Vol. 60, p. 2022 (1988) |
| $^{24}Mg^+$ | 280 | F. Diedrich et al.; Physical Review Letters Vol. 59, p. 2931 (1987; reference 3) |
| $^{88}Sr^+$ | 422 and 1092 | G. P. Barwood et al.; Optics Letters Vol. 18, p. 732 (1993) |
| $^{138}Ba^+$ | 493 and 650 | W. Neuhauser et at.; Applied Physics Vol. 17, p. 123 (1978) |
| $^{199}Hg^+$ | 194 | M. G. Raizen et al.; Physical Review A45, p. 6493 (1992) |
| $^{172}Yb^+$ | 369.5 and 935 | A. S. Bell et al.; Physical Review A44, R20 (1991) |
| $^{40}Ca^+$ | 397 and 872 | J. Vanier and C. Audoin, "The Quantum Physics of Atomic Frequency Standard," Vol. 2, Adam Hilger (1989), pp. 1498–1502 |
| $^{113}Cd^+$ | 226 | J. Vanier and C. Audoin, "The Quantum Physics of Atomic Frequency Standard," Vol. 2, Adam Hilger (1989), pp. 1498–1502 |
| $^{205}Tl^+$ | 191 | J. Helmcke et al.; IEEE Trans. Inst. Meas. Vol. 38, p. 524 (1989) |
| $^{208}Pb^+$ | 369 | J. Helmcke et al.; IEEE Trans. Inst. Meas. Vol. 38, p. 524 (1989) |

According to the invention, using laser-cooled ions as probe ions in the laser cooling setup further improves the sensitivity of detection, as described below.

Consider the case where there are a total of approximately more than 100 and less than $10^6$ trapped probe ions. In such a case, subjecting the trapped probe ions to laser cooling provides very intense fluorescence, because there are many probe ions. This allows a high signal-to-noise ratio to be set, permitting high sensitivity of detection.

In the case above, the energy of the sample ions to be analyzed is largely dissipated by laser cooling and little or no buffer gas cooling is required. Where necessary, a thin helium gas atmosphere at 0.01 Pa or less is sufficient.

Figure 8:
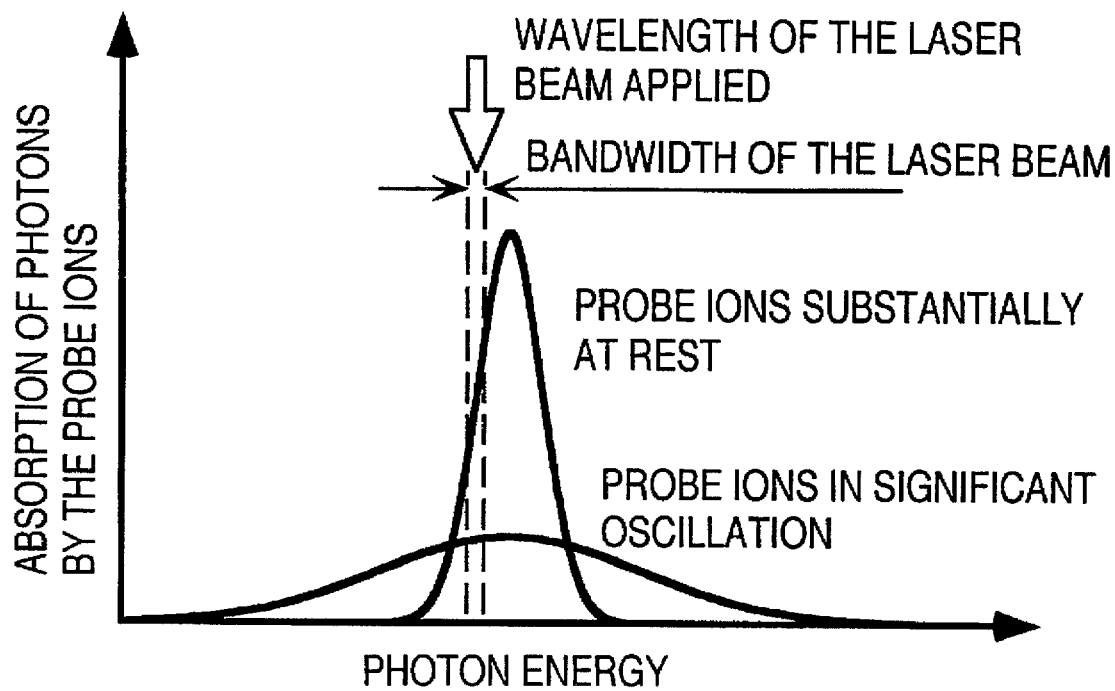
FIG. 8 is a schematic view describing the principles of a yet further method of mass spectrometry according to the invention.

The Doppler cooling method is known to provide the highest laser cooling efficiency and the most intense fluorescence when the wavelength of the laser beam for cooling is red-shifted by half the natural width of the cooling transition of the ion as illustrated in FIG. 8. Likewise, with any one of the above-described first and fourth methods of fluorescent mass spectrometry in use, the wavelength of the cooling laser beam may be shifted by half the ion's natural width toward the longer wavelength side for higher signal intensity which in turn boosts detection sensitivity.

Figure 9:
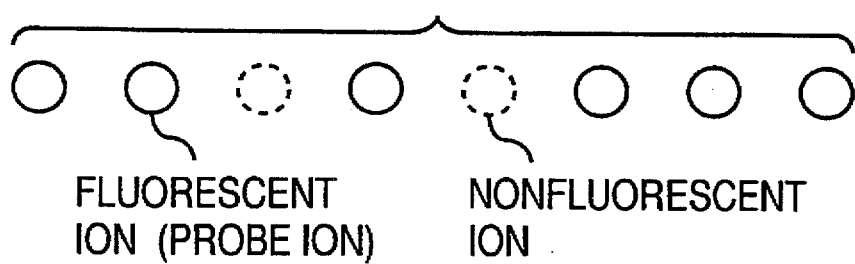
FIG. 9 is a view to help explain another method of mass spectrometry according to the invention.

Consider next the case where a single or a very few ions less than 100 are stored in the ion trap. In that case, laser cooling and sympathetic cooling combine to form a Wigner crystal including the sample ions to be analyzed. When the Wigner crystal is observed as an image, the sample ions appear as lattice vacancies as opposed to the laser-cooled probe ions emitting intense resonance fluorescence, as illustrated in FIG. 9 and shown in FIG. 4 of Waki et al., Physical Review Letters Vol. 68, pp. 2007–2010 (1992; called reference 5 hereunder). Although the nonfluorescent ions cannot be seen directly, their presence is nevertheless apparent wherever there is a lattice vacancy between fluorescent ions in the Wigner crystal state. This makes it possible to know that ions other than the probe ions are included. An AC electric field for analysis is then applied to the ion trap while being scanned in frequency. When the frequency of the AC electric field coincides with the secular frequency of the non fluorescent sample ions in question, they begin to oscillate and disturb the Wigner crystal. The secular frequency of the sample ions is found by detecting the frequency of the analyzing AC electric field in effect when the crystal state starts to be disrupted. The mass-to-charge ratio of the sample ions thus becomes known.

Disturbance of the crystal may be measured in the form of an image by use of imaging means. As the velocity of probe ions increases, they are subject to the Doppler effect. With the probability of light scattering thus reduced, a decline in fluorescence intensity is measured through the use of appropriate means for the purpose.

Figure 20:
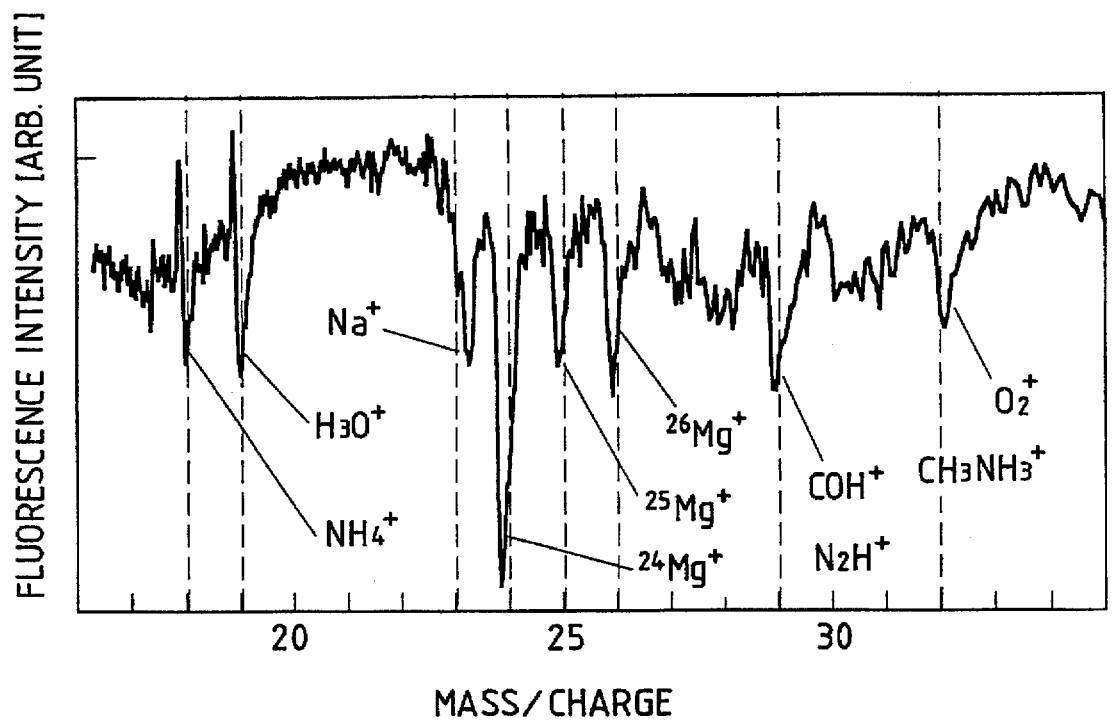
FIG. 20 is a graphic representation depicting another typical mass spectrum detected by the invention.

FIG. 20 illustrates a typical mass spectrum measured by the first method above. This mass spectrum is obtained in a setup where magnesium ions ($^{24}Mg^+$) are used as laser-cooled probe ions and where the sample ions to be analyzed are residual gas ions in a vacuum chamber. After magnesium ions ($^{24}Mg^+$) and vacuum residual gas ions have been stored in the ion trap, the magnesium ions are cooled by applying a laser beam thereto. With fluorescence of high intensity observed, the AC electric field added to the ion trap for analysis is scanned in terms of frequency. The result is the mass spectrum shown illustratively in FIG. 20. Observed in this mass spectrum are ions $^{25}Mg^+$ and $^{26}Mg^+$, i.e., isotope ions of magnesium $^{24}Mg^+$, residual gas ions $O_2^+$, and ion-molecule reaction products $H_3O^+$, $NH_4^+$, $COH^+$, $N_2H^+$, and $CH_3NH_3^+$, i.e., products whose parent ions are the residual gas ions. The number of stored magnesium ions is about 640 including isotope ions having a mass number of 24. When the natural abundance ratios of magnesium ion isotopes with mass numbers of 25 and 26 are taken into account, the number of isotope ions with the mass number of 25 and the number of those with the mass number of 26 are estimated to be about 80 each. With signal intensity taken into consideration, the other ions are also estimated at about 80 in quantity. The results of the inventors' study constitute the basis for the data illustrated in FIG. 20 and are being submitted for publication in the scientific journal "Nature" under the title of "Cooling and Mass-Analysis of Molecules Using Laser-Cooled Atoms" by T. Baba and I. Waki.

Laser-cooled ion types particularly effective when used by the laser cooling scheme of the invention are such heavy ions as $Ca^+$, $Sr^+$, $Cd^+$, $Ba^+$, $Yb^+$, $Hg^+$, $Tl^+$ and $Pb^+$. It is especially effective to use $^{40}Ca^+$, $^{88}Sr^{30}$, $^{114}Cd^+$, $^{138}Ba^+$, $^{174}Yb^+$, $^{202}Hg^+$, $^{205}Tl^+$ and $^{208}Tb^+$ isotopes having high abundance. These ions are preferred because of their heavy masses that can concurrently and stably trap sample ions of large mass numbers within the ion trap.

An example in which barium ions are used will now be described. A radio frequency electric field is applied to the ion trap in such a manner that the value $q_z$ in the equations (1) may vary from 0.5 to 0.9 with respect to barium ions. This setup makes it possible concurrently to trap sample ions having mass numbers up to about 10 times that of barium ions. When the value $q_z$ is selected in the above manner, it becomes possible to subject to mass spectrometry sample ions heavier than barium ions, i.e., those with mass numbers ranging from 100 to 1,000. Conversely, if the radio frequency electric field is applied to the ion trap in such a manner that the value $q_z$ may become close to 0.1, the setup makes it possible concurrently to trap sample ions having mass numbers as low as about one-tenth of that of barium ions. When the value $q_z$ is selected in this manner, it becomes possible to subject to mass spectrometry light sample ions with mass numbers ranging from 10 to 100. If it is desired to put to mass spectrometry sample ions having about the same mass number as that of barium ions, the preferred value $q_z$ regarding barium ions is set approximately between 0.2 and 0.5.

As described, properly adjusting the value $q_z$ for barium ions allows sample ions with mass numbers of 10 through 1,000 to be analyzed by the ion detection methods according to the invention.

In order to make laser sources for laser cooling smaller in size and less expensive, it is advantageous to adopt $Ca^+$, $Sr^+$, $Ba^+$ or $Yb^+$ ions as laser-cooled ions. This is because these ions can be cooled by semiconductor lasers, or by solid state lasers using crystals for second harmonic generation (nonlinear optical crystal; see Table 1). An example in which $Sr^+$ ions are cooled by semiconductor laser is described illustratively in the paper by Barwood et al. listed in Table 1 above.

Described below is an example in which barium ions with a mass number of 138 are utilized. Two kinds of laser are needed to cool barium ions: a laser beam with a wavelength of about 493.2 nm corresponding to the optical transition from level $6^2S_{1/2+ee}$ to level $6^2P_{+e,fra\ 1/2}$, and a laser beam having a wavelength of about 649.9 nm corresponding to the optical transition from level $5^2D_{3/2+ee}$ to level $6^2P_{+e,fra\ 1/2}$. In the past, the laser beams for cooling barium ions used was produced by a large, expensive combination of an argon ion laser device and a dye laser device. It is difficult to incorporate the costly and cumbersome equipment into general-purpose mass spectrometers. This invention solves the above problem by utilizing semiconductor laser devices in a small, inexpensive and high sensitivity mass spectrometry setup.

Since barium ions are known primarily to emit fluorescence having a wavelength of 493.2 nm, the mass spectrometry setup is designed to detect the 493.2-nm wavelength fluorescence.

A first light source to emit a laser beam with the wavelength of 493.2 nm is implemented by use of a single mode semiconductor laser device comprising an illuminant made of a component material InGaAsP, InGaAs or GaAs. The illuminant constitutes a multiple quantum well structure and emits light having a wavelength of 984.4 nm. The frequency of laser oscillation is stabilized on the order of MHz through an external resonator. The laser beam generated by the semiconductor laser is led into a wavelength converter consisting of one of non-linear optical crystals KDP, ADP, $LiIO_3$, $LiNbO_3$, BBO and KTP. Through the wavelength converter, the laser beam with the wavelength of 493.2 nm is ultimately generated.

A second light source to emit a laser beam with the wavelength of 649.9 nm is implemented by means of a distorted multiple quantum well semiconductor laser device comprising a component material AlGaInP.

In fluorescent mass spectrometry using a Paul trap based on the above-described laser cooling scheme, ions lose their energy as a result of laser cooling and come to exist at a high density in a narrow space at the potential bottom of the ion trap. In particular, when the number of ions trapped inside the ion trap is $10^4$ or greater, each ion is strongly affected by the charges of adjacent ions inside the ion trap. The result is a decline in the mass resolution of the ion trapping mass spectrometer.

Figure 10:
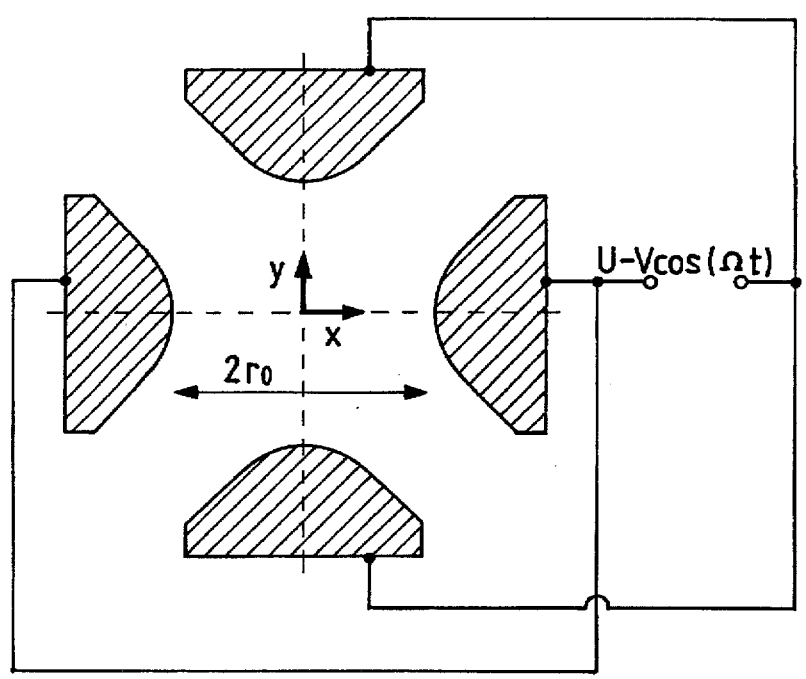
FIG. 10 is a schematic view outlining the structure of a linear quadrupole ion trapping electrode arrangement.
Figure 11:
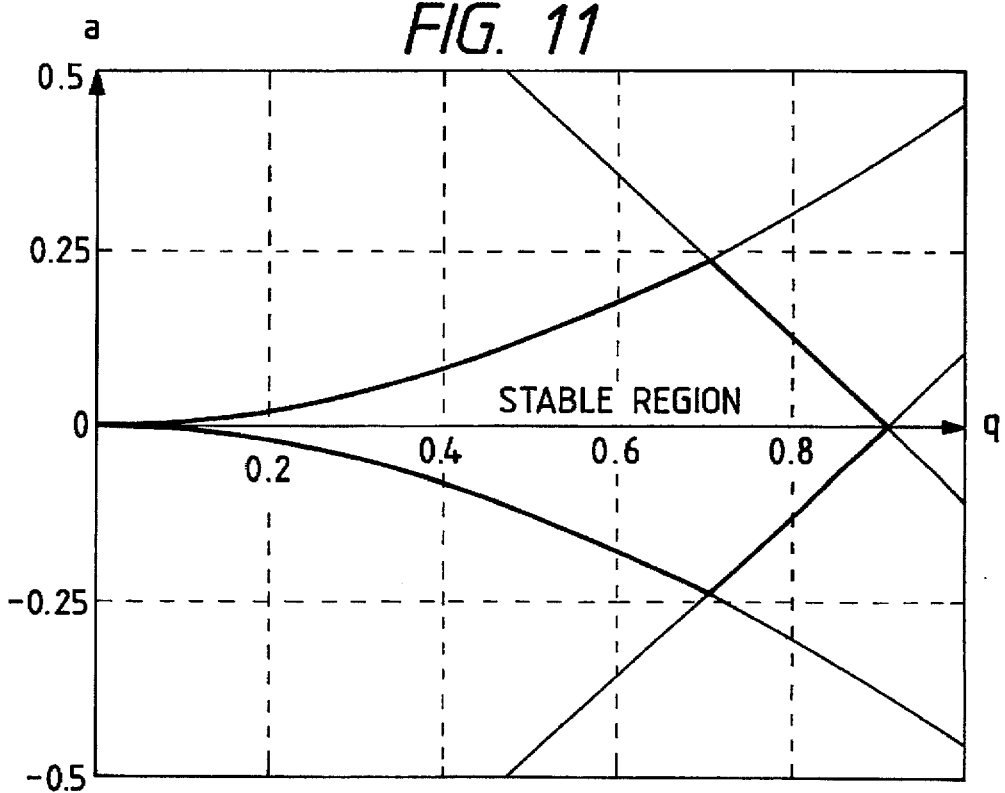
FIG. 11 is a graphic representation showing a region of stability in the linear ion trapping electrode arrangement of FIG. 10.

The deficiency above is circumvented effectively by the invention employing a linear ion trap (discussed in reference 5 and by M. G. Raizen et al., Journal of Modern Optics, Vol. 39, p. 233 (1992)) in place of the Paul trap. FIG. 10 is a cross-sectional view of a typical linear ion trap. Four electrodes, each having a quadrupole structure in its cross section, combine to form the linear ion trapping electrode arrangement. Both ends of the trap are supplied with a DC voltage to avert the leakage of ions therefrom. The region in which ions are stably trapped is the region delineated in thick lines in FIG. 11, expressed using two parameters a and q:

$$a=4QU/(m\Omega^2 r_0^2)$$
$$q=2QV/(m\Omega^2 r_0^2)$$
(6)

The parameters a and q in the equations (6) correspond to their counterparts in the equations (1) given earlier in connection with the Paul trap. Specifically, when a=0, the ions satisfying the relation $$q<0.908$$

are trapped stably in the linear ion trap.

The use of the linear ion trap offers the following advantages: first, the linear ion trap stores ions geometrically linearly inside. That is, the linear ion trap stores numerous ions with their space charge effect drastically reduced compared with the three-dimensional Paul trap. The setup provides a greater dynamic range, which means an improved signal-to-noise ratio for signals to be detected. As a second advantage, a large number of ions are trapped on the center axis in such a manner that they are little exposed to the influence of the trapping radio frequency. By contrast, placing numerous ions into the Paul trap causes ion clouds to disperse away from the trap center. The radio frequency field for trapping ions increases in proportion to the distance from the trap center. This means that the farther from the trap center, the greater the ion heating effect by the ion trapping radio frequency electric field in the Paul trap. By contrast, the linear trap has a reduced ion cloud spreading from the trap center for the same number of ions. This lowers the heating effect by the radio frequency field. With the cooling effect thus enhanced, the linear trap is allowed to have a lower attainable temperature than the three-dimensional trap and provides signal intensity of a higher S/N ratio. A third advantage is an enhanced level of laser cooling efficiency. The enhancement is made possible by radiating the cooling laser beam onto the center axis, whereby a prolonged interactive region is provided between the ions and the laser beam. As a fourth advantage, the laser-cooled ions gather on the center axis, making it easier to observe the ions optically. A fifth advantage is the fact that the linear ion trap is open at both ends. This structure readily affords the linear ion trap direct connection to another linear ion trap or to a mass filter (see PCT/JP/95/01322, filed Jul. 3, 1995, by the applicant of this invention).

The fifth advantage above may be exploited as follows: installing a linear ion trap upstream of the ion trap mass spectrometer makes up a high-precision combination ion trap mass spectrometer. Generally, when probe ions to be cooled by laser are produced, impure ions are also generated concurrently. The impurities tend to impede laser cooling and high-sensitivity detection of fluorescence. In the upstream linear ion trap, laser-cooled probe ions are thus purified until they become free of the impurities. The purified probe ions are cooled efficiently by laser before getting mixed with sample ions in the ion trapping mass spectrometer for analysis.

Although a proposal has been made to apply linear ion trapping to ion trapping mass spectrometry (U.S. Patent No. 4,755,670), the proposed method fails to provide a sufficiently high level of mass resolution for the following reason: as pointed out in the description above, mass resolution is impaired by the need to set up means (i.e., edge electrodes) for applying a DC voltage to both ends of the electrode structure whereby the leakage of ions therefrom is prevented. That is, the DC voltage applied to the edge electrodes generates an non-uniform DC electric field in the lengthwise direction inside the ion trap. This causes the detected secular frequency to have positional dependency. As a result, a sufficiently high level of mass resolution is difficult to attain. This problem is solved by the embodiment of the present invention, by the fluorescence-observing position to the vicinity of the center in the lengthwise direction of the linear trap, away from the end cap electrodes. This efficiently removes signals from the ions that are present in regions where secular frequency varies depending on location.

The embodiment of the invention also resolves the problem above through implementation of laser cooling. With laser cooling carried out, the kinetic energy of the ions inside the ion trap is reduced to the order of mK to K ($10^{-7}$ to $10^{-4}$ eV in terms of energy). It follows that the DC voltage to be applied to the edge electrodes can be very low. This makes mass spectrometry of high resolution feasible through the use of the linear ion trap. What follows is a description of how such an embodiment of the invention is structured and how it is operated.

The two edge electrodes are manufactured in the same shape as the ion trapping electrode arrangement. This makes the three electrode portions identical in capacitance. In consequence, it is easy to align the radio frequency amplitude applied to the three portions. When sample ions and probe ions are being stored inside the linear ion trap, the two types of ions have high levels of kinetic energy and are required to be prevented from leaking out of both ends of the trap under the influence of a substantially high DC voltage. The ions are then cooled by laser. This deprives the ions of their kinetic energy, eliminating the need for applying a high DC voltage to prevent ion leakage from both ends of the ion trap. With laser cooling thus accomplished, the DC voltage may be reduced to a very low level. The DC voltage value should be such that the difference between the secular frequency of the sample ions at the center part in the lengthwise direction inside the linear ion trap electrode arrangement and the secular frequency of the sample ions near the edge electrodes is less than 1 in terms of mass number. This substantially removes the dependency of the sample ions for their secular frequency on position, whereby the linear ion trap realizes mass spectrometry of high resolution.

Figure 14A:
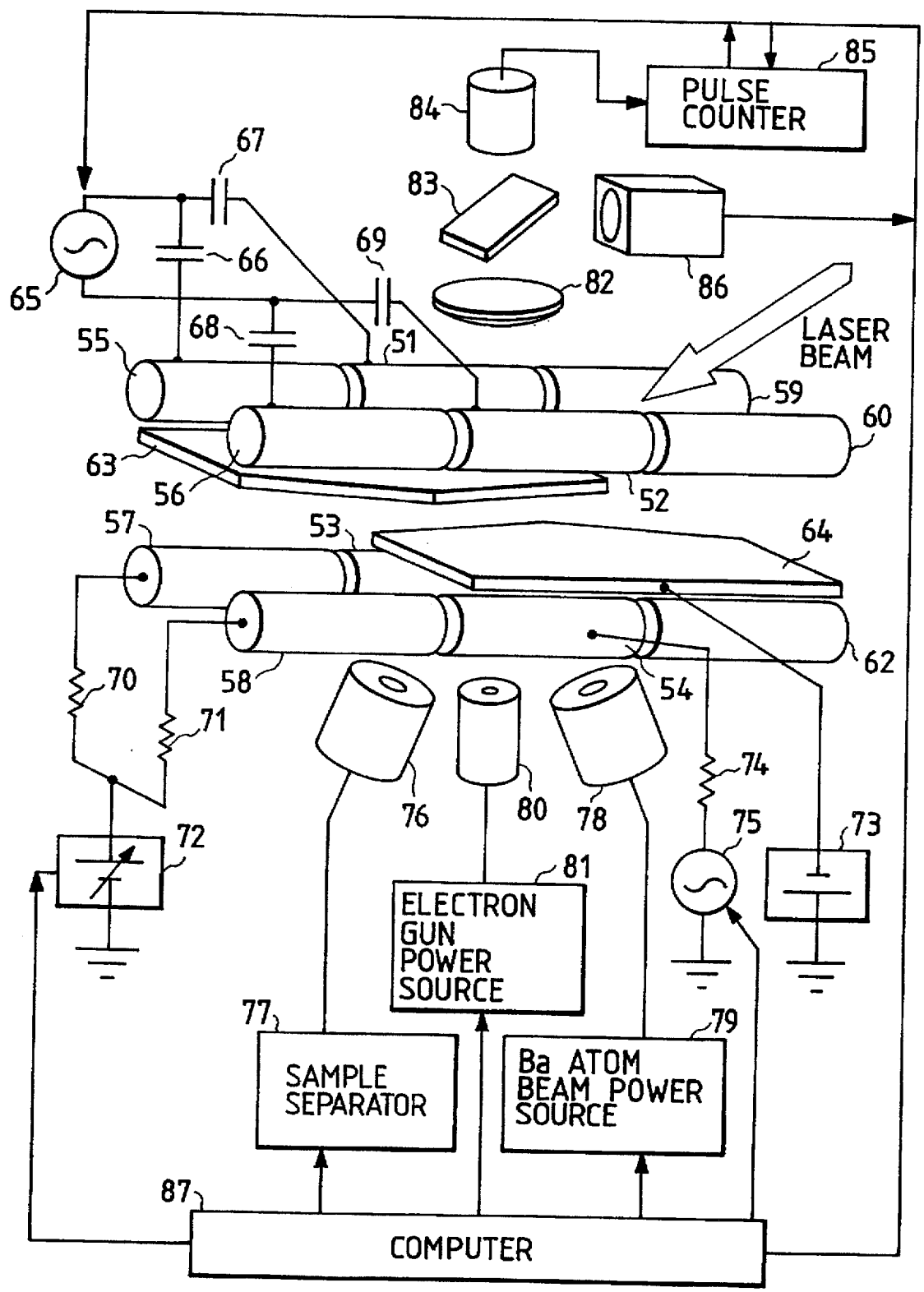
FIG. 14A is a schematic block diagram of another embodiment of the invention.

It is also possible to supplement the linear ion trapping electrode arrangement with an electrode or an electrode pair for creating a spatial potential which would prevent the free movement of ions in the lengthwise direction within the ion trap and attract them toward the center of the lengthwise direction. The added electrode or electrode pair is supplied with a local electric field of very low intensity with its polarity inverse to that of the sample and probe ions. The electrode or electrode pair is shaped so that the added potential may vary gradually in the lengthwise direction. Specifically, the electrode structure is preferably triangular in order to be effective, with the top of the triangle located near the center region of the linear trap and the rest located away from the center axis of the ion trapping electrode arrangement toward the ion trapping electrode edges as shown in FIG. 14A. The voltage value applied is selected to be such that the difference between the secular frequency of the attracted sample ions and that of the unattracted sample ions is sufficiently smaller than 1 in terms of mass number. There are two benefits derived from this setup. One benefit is a reduction of the adverse effects from the DC voltage applied to the edges of the linear electrode structure because the ions are attracted toward the electrode center. The other benefit is an improved level of efficiency in collecting the fluorescence of the probe ions because the ions are attracted toward the electrode center, a location convenient for fluorescence observation.

The fluorescent mass spectrometry according to the invention permits calibration of the mass scale. With the above-described first method of detection in use, causing probe ions in their secular motion to resonate directly in an AC electric field for analysis drastically lowers the intensity of fluorescence. Since the type of the probe ions is known, finding the oscillation frequency at which the probe ions resonate provides a correspondence between the analyzing AC frequency and the mass number. That is, effective means for calibrating the mass scale is obtained.

The fluorescent mass spectrometry according to the invention also permits calibration of the number of sample ions. For the fluorescent mass spectrometry setup of the invention, the number of sample ions detected inside the ion trap ranges from 1 to $10^6$, compared with 100 to $10^6$ in the case of the conventional method of mass selective instability mode operation. Where 100 or more sample ions are to be detected, both the inventive and the conventional methods are used to count the number of ions, and the results are collated for calibration. Since the inventive method is in-situ (in-trap) detection, the calibration is easily achieved by determining firs fly the amount of ions using the inventive method, and then secondly determining the ion quantity using the conventional method. Where the number of sample ions to be counted ranges from 1 to 100, the inventive method allows the absolute number of individual ions to be measured. This means that an absolute calibration of the conventional method is also achieved.

The fluorescent mass spectrometry of the invention may also be applied to achieve in-situ (in-trap) MS-MS mode mass spectrometry. The MS-MS mode mass spectrometry process of the invention involves an in-situ (in-trap) observation. Parent ions are thus observed in an in-situ manner and the ion type is identified keeping the ions trapped. Then the ions are brought into reaction with neutral gases producing daughter and granddaughter ions whose types are also identified. That is, at each of the stages of n-iteration tandem mass spectrometry, products are subjected to mass spectrometry without being ejected out of the trap. This makes it possible to track the types of trapped intermediate ions successively for analysis. The feature serves to determine the structure of high-mass molecules using only a small amount of sample. A single dose of sample, when introduced into the trap, allows MS-MS mode mass spectrometry to be carried out many times.

Where the invention is applied to molecules with mass numbers exceeding 1,000, fluorescent molecules are used as probe ions. Organic scintillator substances are particularly effective. In such cases, the principle of detection is the same as that described above. When probe ions are trapped, the mass number of the fluorescent molecules should be determined by mass spectrometry.

Below is a more specific description of the embodiment outlined above, with reference to the accompanying drawings.

Figure 12:
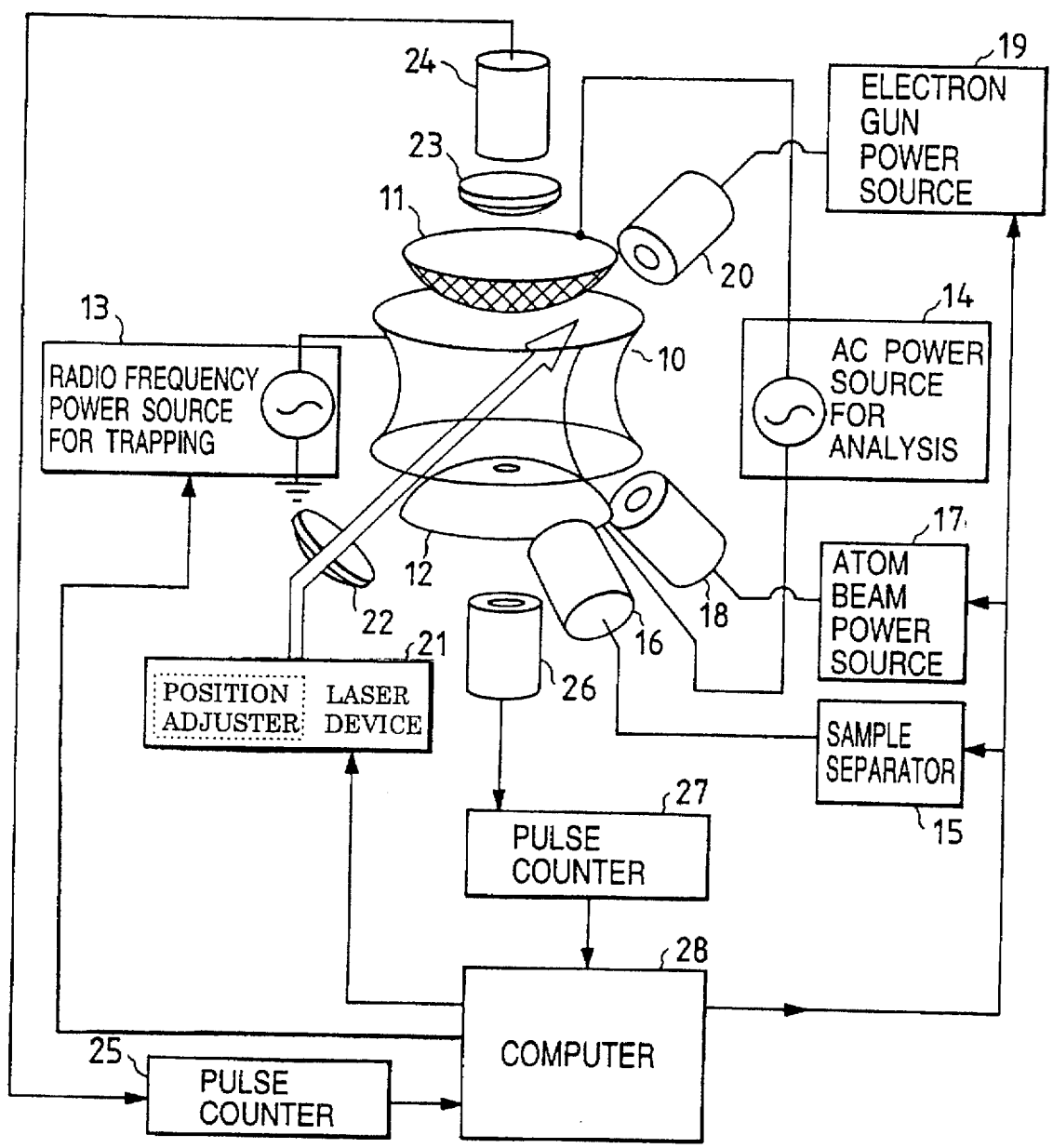
FIG. 12 is a schematic block diagram of one preferred embodiment of the invention.

The embodiment in FIG. 12 uses Paul trap electrodes as its ion trapping electrodes and barium ions as its probe ions.

The embodiment comprises Paul trap electrodes 10 through 12, an ion trapping radio frequency power source 13, an AC power source 14 for analysis, a sample separator 15, a sample beam source 16, a barium atom beam power source 17, a barium atom beam source 18, an electron gun power source 19, an electron gun 20, a laser cooling laser device 21, a lens 22, a light collection device (including objective optics) 23, a photo detector (photomultiplier tube) 24, a pulse counter 25, an ion detector 26, a pulse counter 27, and a computer 28 for control and data accumulation. Of the above components, the ion trapping electrodes 10 to 12, sample beam source 16, barium atom beam source 18, electron gun 20 and ion detector 26 are housed in a vacuum chamber, not shown.

In addition, the laser device 21 includes a position adjuster which adjusts the position of lens 22 in order to adjust an angle or a width of the laser beam introduced to the gap between the ion trap electrodes.

After probe and sample ions are both cooled, simultaneously directly or indirectly, by laser in the embodiment, the analyzing AC voltage is applied to the ion trap while being scanned in frequency. The resulting changes in the intensity of fluorescent light are measured for mass spectrometry.

The ion trapping electrodes are made up of a ring electrode 10 and end cap electrodes 11 and 12. The electrodes are shaped so that a quadrupole electric field is generated inside. Specifically, in a cylindrical coordinate system where the axial direction of rotation is taken on the z axis and the radial direction of rotation is on the r axis, the electrode surface is manufactured to a shape expressed by the following equation (7):

$$r^2 - 2z^2 = r_0^2 \qquad (7)$$

The cross-sectional view of the electrodes is shown in FIG. 1. The radius $r_0$ may be set between 5 mm and 25 mm. The embodiment has the radius $r_0$ set for 10 mm. The end cap electrode 12 is made of a metal mesh permitting light to pass through. The end cap electrode 12 has at its center a through hole allowing ions to be ejected from inside the ion trap.

A trapping radio frequency voltage is applied to the ion trap as follows: the two end cap electrodes 11 and 12 is connected to ground potential relative to a radio frequency voltage, whereas the radio frequency power source 13 is used to feed the radio frequency voltage to the ring electrode 10. The radio frequency voltage produces a quadrupole radio frequency electric field inside the ion trapping electrodes, thereby trapping ions in a three-dimensional manner. In this embodiment, the radio frequency is set to 500 kHz for ease of implementation. To select the $q_z$ value between 0 and 0.908 for barium ions, which are the probe ions of this embodiment, requires setting a radio frequency amplitude ranging from 0 to 450 V, as defined by the equations (1).

As mentioned, the above embodiment uses barium ions as its probe ions. The radio frequency amplitude is adjusted in accordance with the mass number of sample ions to be analyzed. With the $q_z$ value set to 0.1 for barium ions, the embodiment can simultaneously trap ions ranging from those approximately equal in mass number to the barium ions to those with about one-tenth of the mass number of the barium ions. In such a case, the applicable masses of sample ions to be analyzed range approximately from 10 to 150. Where the $q_z$ value is set to 0.9 for barium ions, it is possible for the embodiment simultaneously to trap ions with a mass number up to 10 times that of barium ions. In that case, the applicable masses of sample ions to be analyzed range approximately from 140 to 1,000.

The radio frequency power source 13 to provide the radio frequency voltage is an LC resonance circuit. The LC resonance circuit is constituted by use of the ion trapping electrode 10 as a capacitor to which the secondary coil of a radio frequency step-up transformer is connected. The resonance frequency of this circuit is set to 500 kHz. The LC resonance circuit is resonated by radio frequency power having the frequency of 500 kHz and input from the primary coil of the radio frequency step-up transformer. The applied radio frequency amplitude is adjusted by varying the value of the input radio frequency power.

The end cap electrodes 11 and 12 are connected to ground potential relative to the radio frequency of 500 kHz in effect, as described. Between the two end cap electrodes 11 and 12, an AC voltage for analysis (400 kHz or less) is applied by means of the analyzing AC power source 14. The Q value of the AC power source 14 needs to be held low. This is attributable to the need to minimize the dependency of the amplitude of the analyzing AC voltage on frequency when the AC voltage is scanned in terms of frequency.

Barium ions, which are the probe ions of the embodiment, are produced by radiating an electron beam to a barium atom beam for ionization inside the ion trap. The electron gun 20 generates the electron beam by accelerating thermions, created from heating of a tungsten filament, through the use of a DC current potential difference of 100 V. The electron beam thus generated is converged by a Wehnelt electrode structure. The electron beam is switched on and off by applying or removing the accelerating voltage. The barium atom beam source 18 is structured to guide into the ion trap the barium gas generated by heating a barium metal piece. A shutter, furnished to the barium atom beam source 18, is opened and closed to control the introduction of a barium atom beam into the ion trap. The shutter is kept closed except when barium ions are produced, so as to prevent the electrodes from getting contaminated by barium atoms and to avert the mixing of barium ions when sample atoms are introduced into the trap.

Sample ions are subjected to preprocessing by the sample separator 15 wherein the molecules to be analyzed are separated. The sample thus refined is sent to the sample beam source 16. The sample separator 15 may be a gas chromatograph, a liquid chromatograph or the like. The sample beam source 16 is equipped with a shutter and thereby controls the incidence of a sample molecular beam as needed. The sample introduced into the ion trap is subjected to the radiation of the electron beam from the electron gun 20, whereby the sample ions to be analyzed are produced. In this setup, the energy of the electron beam ranges from 10 to 200 electron volts. An optimum electron voltage is selected so that the sample ions are maximally protected against destruction.

The laser device 21 generates cooling laser beam for cooling the barium ions. Two kinds of laser are needed for the purpose of cooling: one with a wavelength of 493.4 nm and the other with a wavelength of 649.9 nm. The embodiment uses two ring dye laser devices in combination as the cooling laser source. References in Table 1 may be referred to when the laser device is implemented. The ring dye laser devices may be replaced by semiconductor laser devices. In particular, the laser device for generating laser with the wavelength of 493 nm should be optically stable with a frequency stability of 1 MHz and should be capable of scanning optical frequencies up to 10 GHz.

The laser beam is introduced by way of the gap between the ion trap electrodes and through the lens 22. The angle of incidence of the laser beam is 55 degrees with respect to the z axis. The laser beam serves both to cool and to excite the probe ions, as discussed earlier. The position of the lens 22 is adjustable along the laser beam and within the plane perpendicular to the laser beam with the focal length and the position of the lens 22 chosen appropriately, any one of the above-described first through fifth methods of fluorescent mass spectrometry is carried out. That is, when the first method of FIG. 4 is to be implemented, the lens 22 is moved so that the beam waist of the finely focused laser beam is located at the center of the ion trapping electrodes. When the second method shown in FIG. 5 is to be implemented, the lens 22 is moved so that the laser beam is focused broadly for widespread laser illumination into the ion trap. Where the third method illustrated in FIG. 6 is to be implemented, the lens 22 is moved so that the beam waist of the finely focused laser beam is located about 1 mm off the center of the ion trap electrodes. Where the fourth method depicted in FIG. 7-1 is to be implemented, the laser beam arrangement is made as shown in FIG. 4 or 5. Where the fifth method indicated in FIG. 7-2 is to be implemented, the beam arrangement is made as illustrated in FIG. 5 or 6.

Below is a description of an example in which, with the beam arrangement of FIG. 4 in place, laser cooling is carried out.

The light collection lens 23 and photomultiplier tube 24 are used as light detecting means for observing changes in fluorescence intensity. An interference filter is set up immediately before the light-receiving surface of the photomultiplier tube 24 to let light having the wavelength of 493.4 nm pass through selectively. The light collection lens 23 and photomultiplier tube 24 are arranged so that the interior of the ion trap may be observed through the metal mesh type end cap electrode 11. The photomultiplier tube 24 generates pulses which are counted by the pulse counter 25.

In addition to the arrangement above, the embodiment has the ion detector 26 set up so that ions ejected through the hole of the end cap electrode 12 may also be detected in the conventional mass selective instability mode. The pulses generated by the ion detector 26 are counted by the pulse counter 27.

The computer 28 controls frequency-related operations of the radio frequency power source 13, analyzing AC power source 14 and laser device 21. The computer 28 also controls the following items: the operation of the atom beam power source 17, sample separator 15 and electron gun power source 19; the processing of the results of pulse counts; and the separation of $\omega z$ and $\omega r$ discussed earlier.

Figure 13:
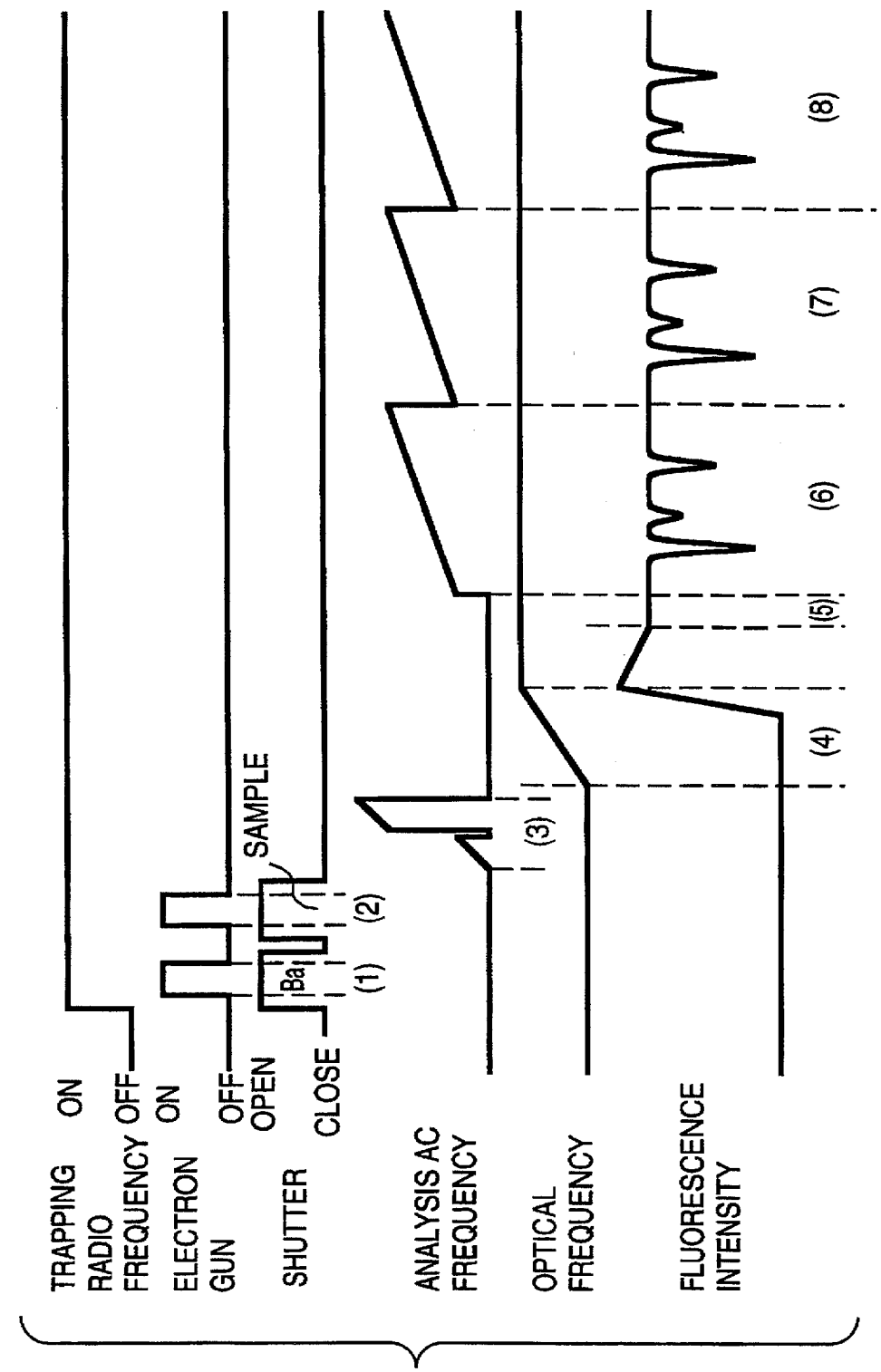
FIG. 13 is a timing chart in effect when the embodiment of FIG. 12 is in operation.

How the above embodiment is operated will now be described with reference to FIG. 13. Initially, the shutter of the barium atom beam source 18 is switched on and off at time (1) to introduce barium into the ion trap. The electron gun 20 ionizes the barium so that the probe barium ions are stored in the ion trap. The shutter of the sample beam source 18 is switched on and off at time (2) to introduce sample into the ion trap. The electron gun 20 ionizes the introduced sample to be analyzed so that sample ions are stored in the ion trap. At time (3), the background ions not to be analyzed are ejected from the ion trap. This is readily accomplished as follows: the analyzing AC voltage circuit 14 applies an AC voltage having the same frequency as the secular frequency of the background ions across the two end cap electrodes 11 to 12. The applied AC voltage causes the background ions to resonate and jump out of the ion trap. With the background ions thus removed, the ions comprising the sample and probe ions is subjected to the radiation of a laser beam for cooling purposes at time (4). At this point, cooling proceeds efficiently if the laser beam frequency is scanned from the long to the short wavelength side. The cooling process deprives the ions of their kinetic energy and reduces the width of the scattering spectrum that was broadened before cooling due to the Doppler effect. The probe ions then emit intense resonant scattering light (fluorescence). When such resonant scattering light becomes observable, the laser beam wavelength in effect is fixed at that point. A wait state then intervenes until the ions reaches its thermal equilibrium state and its fluorescence intensity is stabilized at time (5). At time (6), the AC voltage is applied across the two end cap electrodes 11 to 12. When the frequency of the applied AC voltage coincides with the oscillation frequency of the sample ion species to be analyzed, the ion species absorbs energy and raises its temperature. This in turn broadens the width of the light scattering (fluorescence) spectrum. In the state where the laser beam wavelength is fixed, the broadening of the scattering spectrum is observed as a drop in fluorescence intensity. The phenomenon is detected by the photomultiplier tube 24, sensing the presence of the sample ions. In FIG. 13, the detecting procedure is repeated at times (7) and (8).

Major noise sources affecting the mass spectrometry by the embodiment are: instability of the intensity and optical frequency of the laser beam, and instability of ions in cloud and crystal phases. The adverse effects are reduced by a number of ways. For example, the analyzing AC power source is modulated in amplitude so that the amount of optical intensity modulation is detected synchronously. Alternatively, optical intensity is detected synchronously with the secular frequency of barium or of sample ions. Synchronous detection is easily implemented by use of a lock-in amplifier.

Furthermore, the ion detection method of this embodiment is used to calibrate absolute ion counts obtained in the conventional mass selective instability mode. Because the inventive ion detection method involves an in-situ observation, the number of sample ions to be analyzed is first determined by the embodiment. Then the number of the sample ions is counted in the mass selective instability mode, and the results from the two methods are collated for calibration.

Figure 14B:
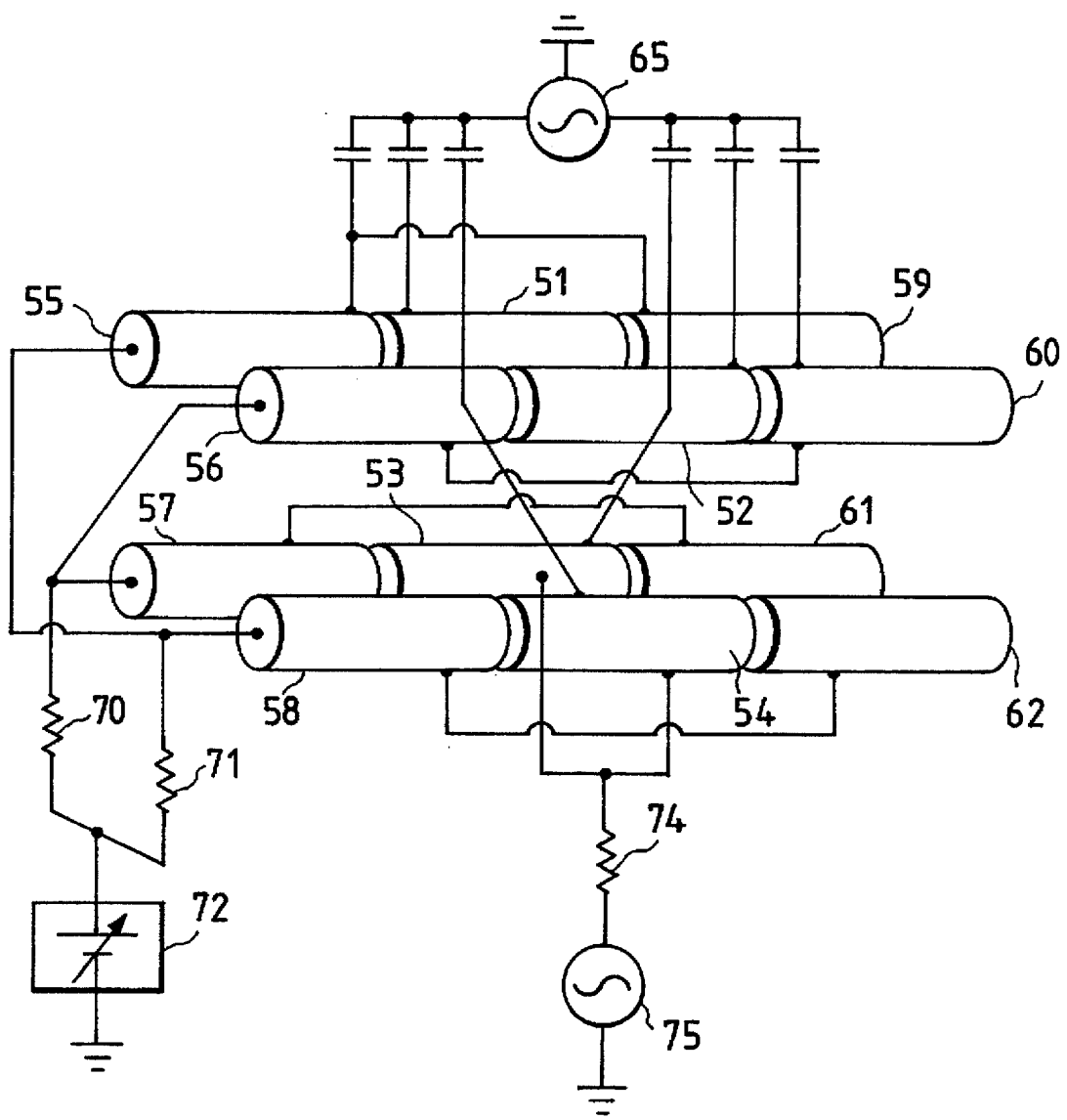
FIG. 14B is a wiring diagram showing the wiring for voltages applied to the electrodes of FIG. 14A.

Described below with reference to FIGS. 14A and 14B is another embodiment in which the linear ion trap is used as a mass spectrometer detecting a very limited number of ions (i.e., one to 100).

As shown in FIG. 14A, the embodiment comprises linear ion trapping electrodes 51 through 54, end electrodes 55 through 58 and 59 through 62 (electrode 61 is not shown in FIG. 14A), plate electrodes 63 and 64, a plate electrode DC power source 73, an ion trapping radio frequency power source 65, capacitors 66 through 69, high-impedance wiring resistors 70 and 71, a DC voltage power source 72, a high-impedance wiring resistor 74, an analyzing AC power source 75, a sample beam source 76, a sample separator 77, a barium atom beam source 78, a barium atom beam power source 79, an electron gun 80, an electron gun power source 81, a cooling laser device (not shown), an objective lens 82, a semi-transparent mirror 83, a photo detector (photomultiplier tube) 84, a pulse counter 85, an ultra-sensitive image-intensified camera 86, and a computer 87 for control and data collection. Of these components, the linear ion trapping electrodes 51 through 54, two sets of end electrodes 55 through 58 as well as 59 through 62, two plate electrodes 63 and 64, sample beam source 76, barium atom beam source 78 and electron gun 80 are housed in a vacuum chamber. In FIG. 14A, many connecting lines are omitted for purpose of simplification and illustration. Detailed connections associated with the linear ion trapping electrodes are shown in separately FIG. 14B. The lines connecting the computer 87 to other components indicate signal exchanges therebetween.

The linear ion trap proper includes the linear ion trapping electrodes 51 through 54, and the two sets of end electrodes 55 through 58 as well as 59 through 62 for preventing ion leakage from the trap. The cross-section of the quadrupole structure on the trap interior side is a quadrupole structure constituted by the surface expressed by the equation (8) below. The equation (8) shows that the cross-section of the electrode structure is hyperbolic. As in the embodiment of FIG. 13, the electrodes 51 and 52 are of a mesh structure substantially allowing light to pass through. This structure enhances the light collection efficiency of the objective lens 82. In FIG. 14, the electrodes are sketched as cylinders for purpose of simplification. The equation is given as $$x^2 - y^2 = r_0^2 \qquad (8)$$

where, $r_0$ is selected between 5 and 20 mm. With this embodiment, $r_0$ is set to 10 mm. The length of the electrodes in the linear ion trap is selected between 50 mm and 100 mm. With this embodiment, that length is select to be 50 mm. The trap electrodes and the end electrodes are shaped to be sufficiently longer than $r_0$ so that the electric field will not be distorted in the linear ion trap. With this embodiment, the length of the end cap electrodes is set to 50 ram, the same as the length of the ion trapping electrodes. This renders the three electrode portions identical in capacitance and makes it easy to apply a radio frequency of the same amplitude to the ion trap electrodes and end electrodes.

To trap the ions, identical radio frequency voltages of $V\cos(\Omega t)/2$ and $-V\cos(\Omega t)/2$ relative to the earth potential are applied to the ion trap and to the two sets of end electrodes in a diagonally paired manner with equal phases. The two sets of end electrodes are fed with the DC voltage through high resistance to prevent ion leakage. As with the previous embodiment, the radio frequency power source is implemented by use of an LC resonance circuit. The AC voltage for analysis is supplied through high impedance with respect to the ground potential (an electric resistor on the megaohm order) to the electrodes 53 and 54. The analyzing AC voltage is sufficient when applied to the electrodes with an amplitude of 1 mV or less.

In addition to the above-described electrode structure and driving power sources, this embodiment has the plate electrodes 63 and 64 installed for attracting trapped ions toward the electrode center inside the linear ion trap. The plate electrodes 63 and 64 are shaped so as to generate a potential whereby the trapped ions are drawn toward the center of the linear ion trap in its lengthwise direction. With this embodiment, the pentagon-shaped electrodes 63 and 64 are placed symmetrically in a gap between the quadrupole electrodes, with the vertices of the pentagons positioned opposite to one another near the center of the linear ion trap in its lengthwise direction, as illustrated. The plate electrodes are each separated from the electrode center axis by about $r_0$ so that they are in parallel with a plane formed by the ion trapping electrodes 51 and 52 and are symmetrical to each other around the electrode center axis, are in a plane containing that axis. The two plate electrodes are supplied with a very small negative DC voltage of about −1 mV from the DC voltage source 73.

The sample beam source 76, barium atom beam source 78 and electron gun 80 for generating sample and probe ions, as well as the light source arrangement, not shown, for generating laser beams for cooling barium ions may be the same as those of the previous embodiment. For the fluorescence detecting arrangement, this embodiment supplements the photomultiplier tube (photo detector 84) of the previous embodiment with the ultra-sensitive image-intensified camera 86 for detecting fluorescence as an image. These components are controlled by the computer 87.

This embodiment is operated illustratively as follows: initially, the end electrodes are fed with a voltage of 1 V or more. Ions are being stored into the ion trap in this state. The operating procedure up to the steps for storing sample and probe ions before the start of laser beam radiation is the same as that of the previous embodiment. The laser beam is introduced into the linear trap along the axis.

With probe ions added to the sample ions to be analyzed, the ions are subjected to an intense laser cooling process. Sufficient cooling of the ions deprives them of their kinetic energy to such an extent that a high end electrode voltage is no longer necessary. This voltage, now set by the embodiment to about 1 mV after cooling, is low enough to ensure uniform secular frequencies in the ion trap. At this stage, the ions are attracted gently toward the electrode center by the plate electrodes 63 and 64.

The laser-cooled ions turn into a Wigner crystal state in which the ions are arranged into a lattice pattern. An observation by camera of the resonance scattering light reveals that the laser-cooled barium ions emit intense fluorescence; they are observed as a fluorescent lattice point each. On the other hand, the sample ions not cooled by laser do not emit fluorescence and are observed as lattice vacancies, as explained above with reference to FIG. 9. Finding the presence of lattice vacancies provides a means to count individual sample ions starting from one. The type of the sample ions is identified in the same manner as with the previous embodiment, i.e., by applying to the ion trap the analyzing AC voltage while it is scanned in frequency. Specifically, when the secular frequency of the sample ions coincides with the frequency of the analyzing AC voltage, the crystal lattice of the ions is disturbed. The disturbance appears in the form of changes in the optical intensity, spatial distribution and oscillation frequency of each of the crystal lattice probe ions. Individual crystal probe ions are then observed by camera for such changes, and one of the first through fifth methods of fluorescent mass spectrometry above is used to identify the type of the sample ions in question.

Figure 15:
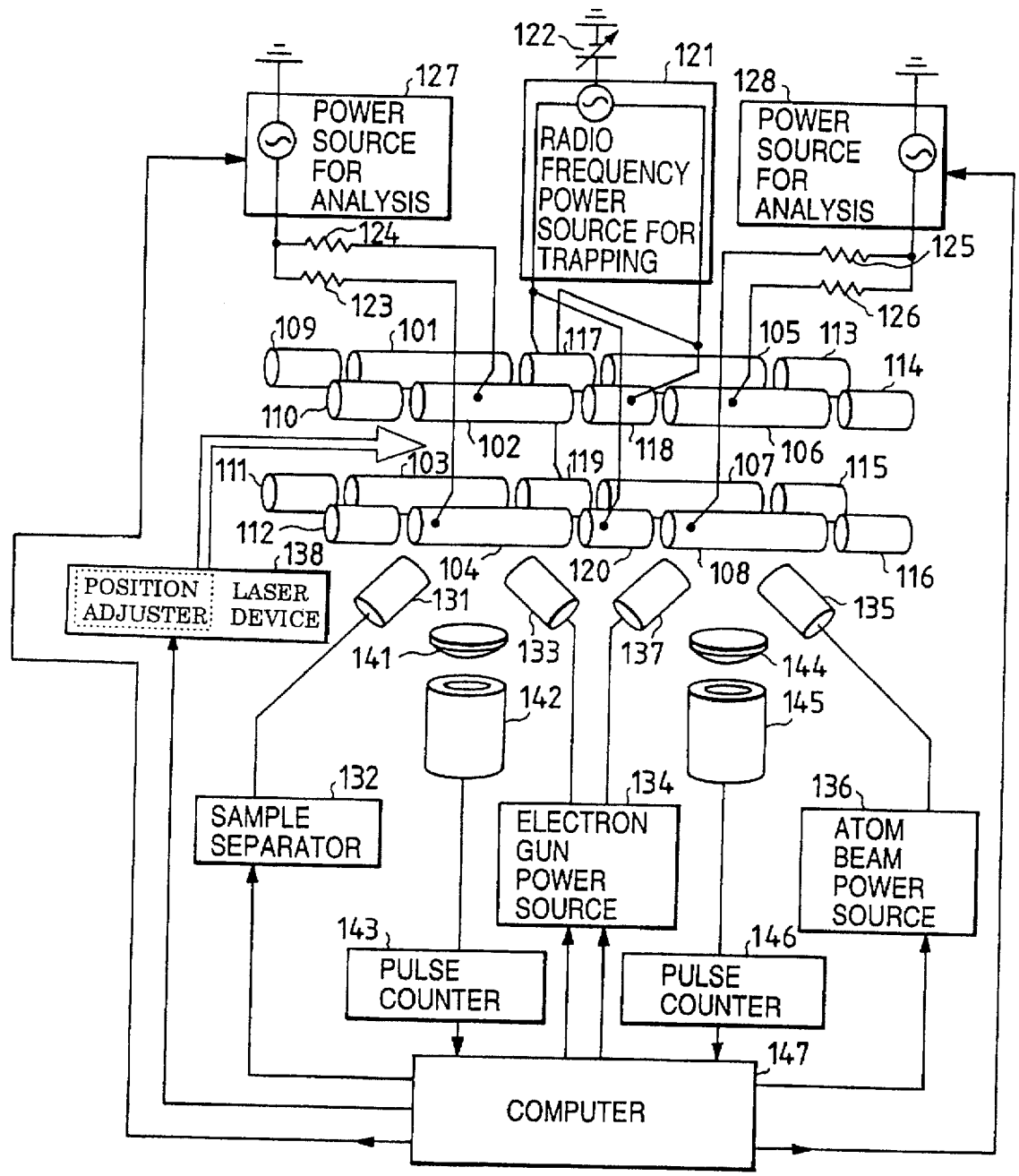
FIG. 15 is a schematic block diagram of a further embodiment of the invention.

Descried below with reference to FIG. 15 is another embodiment having two linear ion traps coupled in a cascade connection. In this embodiment, probe ions are cooled in preparation for mixture with sample ions for producing cold probe ions efficiently.

The ion trapping electrodes of this embodiment comprise a sample ion trapping region made of electrode portions 101 through 104, a laser-cooled ion trapping region of portions 105 through 108, end electrode regions of portions 109 through 112 as well as 113 through 116, and a dividing region of portions 117 through 120. Each region constitutes a quadrupole electrode structure made up of four electrode portions. Each region is furnished with a radio frequency power source for feeding radio frequencies of a desired amplitude to the region and with a DC power source for supplying a DC voltage to the region. In FIG. 15, a radio frequency power source 121 and a DC power source 122 for the dividing region alone are shown for purpose of simplification. In practice, the power source arrangement of the same structure is also connected to the sample ion trapping region, laser-cooled ion trapping region and two end electrode regions.

The sample ion trapping region and laser-cooled ion trapping region have a mass spectrometry function each. Thus analyzing AC power sources 127 and 128 are connected to each of the two regions via high-impedance connecting means (i.e., high resistances) 123 through 126. This setup creates a dipole electric field inside the sample ion trapping region and laser-cooled ion trapping region.

The sample ion trapping region is furnished with a sample separator 132, a sample beam source 131, an electron gun 133 and an electron gun power source 134. The laser-cooled ion trapping region is provided with a barium atom beam source 135, a barium atom beam power source 136, an electron gun 137 and the electron gun power source 134. Cooling laser beams are generated by a laser device 138. The beam sources, electron guns and laser device of this embodiment may be the same in detail as those of the embodiment in FIG. 12. Two detection optics are provided: one comprising a lens 141, a photomultiplier tube 142 and a pulse counter 143 for detecting fluorescence in the sample ion trapping region; the other including a lens 144, a photomultiplier tube 145 and a pulse counter 146 for observing the laser-cooled ion trapping region. The sample separator and the two sets of analyzing power sources, of electron beam sources, and of electron guns are controlled by the computer 147. The computer 147 also controls the laser device in operation and the pulse counters in processing the pulse counts made. The electrode portions 103, 104, 107 and 108 have holes allowing light to pass through. This helps to improve the light collection efficiency of the lenses 141 and 144.

Figure 16:
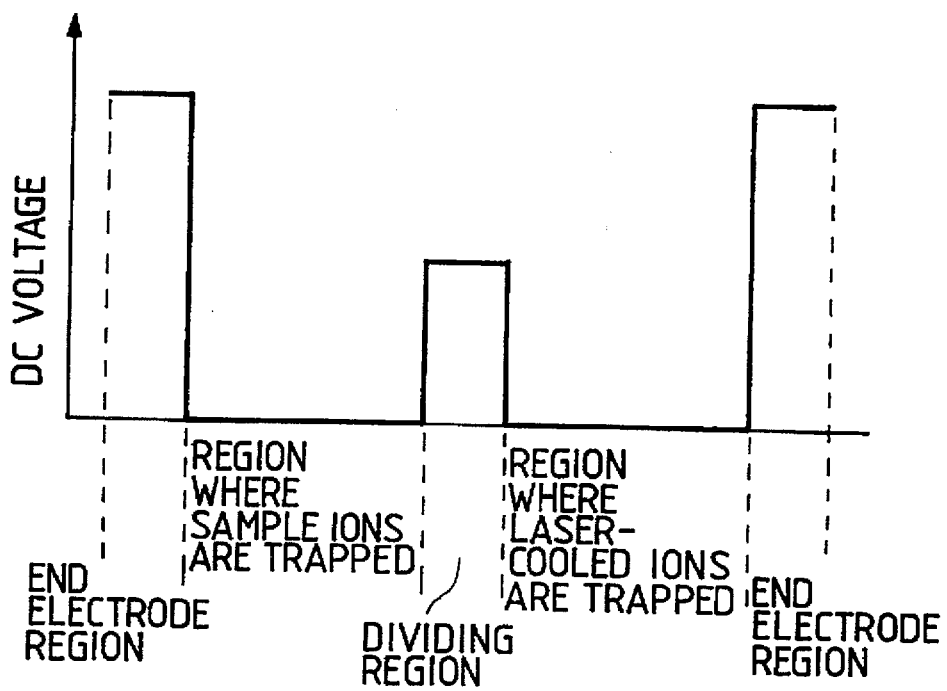
FIG. 16 is a graphic representation depicting one kind of operation of the embodiment in FIG. 15.

How this embodiment is typically operated will now be described. Initially, ions are stored. At this point, as shown in FIG. 16, the two end electrode regions are fed with a DC voltage sufficiently higher than those for other regions. This is to prevent the leakage of trapped ions from the end electrode portions. The dividing region is supplied with a DC voltage higher than that fed to the two ion trapping regions so that ions will not migrate between the two regions. Sample ions are trapped in the sample ion trapping region, and laser-cooled ions are trapped in the laser-cooled ion trapping region.

After the ions have been stored, background ions are removed from the sample ion trapping region so that the sample ions alone are left therein. Background ions are removed as follows: at time (3) in FIG. 13, the analyzing AC voltage 127 is applied to the sample ion trapping region while the voltage is being scanned over a frequency range excluding the secular frequency of the sample ions. The scanning is performed with an amplitude large enough to eject the background ions from the sample ion trapping region. In the laser-cooled ion trapping region, background ions are also removed so as to leave the laser-cooled ions alone inside. The process of background ion removal involves applying the analyzing AC voltage 128 to the laser-cooled ion trapping region while the voltage is being scanned over a frequency range excluding the secular frequency of the laser-cooled ions. The scanning is performed with an amplitude large enough to eject the background ions from the laser-cooled ion trapping region.

A cooling laser beam is then radiated along the trap axis to cool the ions in the laser-cooled ion trapping region. This process constitutes preliminary cooling of the probe ions. Thereafter, as with the mass spectrometry setup of FIG. 12, the analyzing AC voltage is applied to the probe ions while the voltage is being scanned in frequency. The spectrum of the fluorescence from the probe ions is checked to see if they contain any impure ions.

Figure 17:
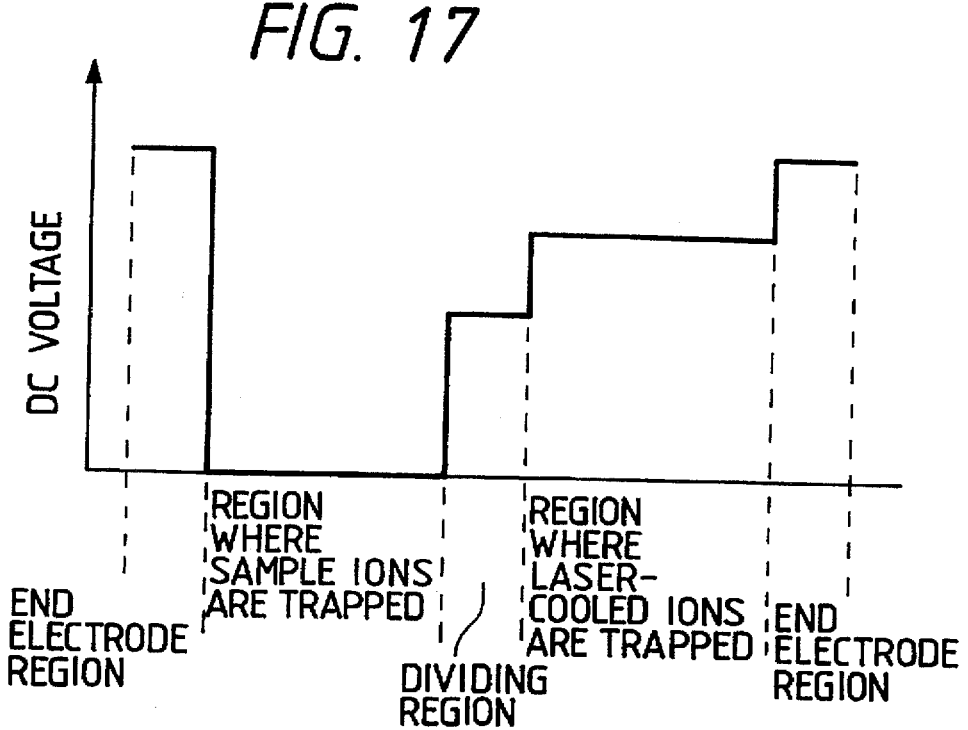
FIG. 17 is a graphic representation illustrating another kind of operation of the embodiment in FIG. 15.

After the absence of impure ions is verified, the DC voltage fed to the laser-cooled ion trapping region is raised to a level higher than the DC voltage supplied to the dividing region, as shown in FIG. 17. In this state, all the ions in the sample ion trapping region are cooled by laser, either directly or sympathetically, whereby a thermal equilibrium state is reached between the probe and sample ions. Then the analyzing AC voltage field of the sample ion trapping region is scanned in frequency to obtain a mass spectrum of the sample ion in question. The operating procedure at this stage is the same as that of the embodiment in FIG. 12.

What follows is a description of how to carry out mass spectrometry based on the in-trap n-iteration tandem mass spectrometry method using the two linear ion traps coupled in cascade connection as shown in FIG. 15.

As with the above embodiment, sample ions are stored, mixed with probe ions, and the mixture is cooled by laser radiation. After the cooling, the quantity of existing parent ions, which are the sample ions to be analyzed, is ascertained by observing the intensity of scattering light of the probe ions.

With the quantity of parent ions thus measured, the q value with respect to these parent ions is set to as small as about 0.1 or less. Then the analyzing AC voltage circuit is used to apply the secular frequency of the parent ions to the ion trap. This causes the parent ions to oscillate by resonance and break up through collision with neutral molecules ambient gas especially introduced for the purpose. The mass spectrum of daughter ions from such destruction is detected by the in-situ ion detecting method using laser cooling. Thereafter, some daughter ions are selected specifically for further destruction followed by mass spectrometry. This allows the in-trap n-iteration tandem mass spectrometry method to verify the mass spectrum at each of multiple stages in a real-time, in-situ manner, until the mass spectrum of the last stage is acquired. Compared with conventional out-of-trap detection methods, the n-iteration tandem mass spectrometry method when carried out as described effectively permits precise and quick mass spectrometry using only a small dose of sample.

In the embodiments above, the procedure for obtaining the mass spectrum of sample ions was described as that for scanning the analyzing electric field in terms of frequency. In this respect, it is possible to utilize an analyzing AC electric field encompassing the secular frequencies of many kinds of sample ions. Such a setup is implemented illustratively by applying white noise or pulse voltages to the ion trapping arrangement. Detected signals representing the time profile of the intensity of the fluorescence emitted by the sample ions are then subjected to Fourier transformation. This makes it possible to detect the secular frequencies and quantities of many kinds of sample ions in a single run of mass spectrometry.

As many apparently different embodiments of this invention may be made without departing from the spirit and scope thereof, it is to be understood that the invention is not limited to the specific embodiments thereof except as defined in the appended claims.

What is claimed is:

1. An ion trapping mass spectrometry method for use with an electrode structure so as to generate an ion trapping field constituting an ion trapping region, said ion trapping region trapping sample ions which are analyzed through oscillation by resonance with a frequency of an analyzing AC electric field applied to said ion trapping field, said ion trapping mass spectrometry method comprising the steps of:

(a) trapping probe ions and said sample ions inside said ion trapping region, the mass-to-charge ratio of said probe ion being known;

(b) radiating a laser beam of a predetermined wavelength to said probe ions, thereby causing said probe ions to emit fluorescence through optical excitation; and (c) causing said analyzing AC electric field to act on said sample ions;

wherein, when said sample ions oscillate depending on the mass-to-charge ratio thereof under the influence of said analyzing AC electric field, the oscillating sample ions interact with said probe ions in a Coulomb collision leading to kinetic changes of said probe ions inside said ion trapping region, said kinetic changes resulting in scattered fluorescence changes which are detected to verify the presence of said sample ions.

2. An ion trapping mass spectrometry method according to claim 1, wherein the frequency of said analyzing AC electric field is varied over time to obtain the mass spectrum of said sample ions.

3. An ion trapping mass spectrometry method according to claim 2, wherein a finely focused laser beam for exciting said probe ions is radiated to a center of ion trapping electrodes forming said ion trapping region in order to excite said fluorescence of said probe ions, the resonating sample ions broadening the velocity distribution and spatial distribution of said probe ions so as to reduce the number of probe ions existing inside the radiated laser beam resulting in a decline in the intensity of said fluorescence, said decline being detected as changes in fluorescence intensity.

4. An ion trapping mass spectrometry method according to claim 2, wherein a broadly focused laser beam for exciting said probe ions is radiated to a wide area of said ion trapping region around a center of ion trapping electrodes forming the ion trapping region in order to excite said fluorescence of said probe ions, the spatial distribution of said probe ions broadened by Coulomb collision with said resonating sample ions, the broadened spatial distribution being detected as an image.

5. An ion trapping mass spectrometry method according to claim 2, wherein said laser beam for exciting said probe ions is radiated into said ion trapping region but off a center of ion trapping electrodes forming the ion trapping region, and wherein said sample ions are resonated to broaden the spatial distribution of said probe ions which emit fluorescence when subjected to the exciting laser beam, thus said fluorescence being increased which is detected so as to find changes in the spatial distribution of said probe ions.

6. An ion trapping mass spectrometry method according to claim 2, wherein said probe ions are those with a narrow fluorescent spectral bandwidth, and wherein monochromatic light having a wavelength substantially the same as a center wavelength of the fluorescence spectrum of said probe ions and having a degree of monochromaticity narrower than a width of the fluorescence spectrum of said probe ions is radiated to excite the fluorescence of said probe ions whose velocity distribution is broadened through the resonance of said sample ions, the broadening of said velocity distribution of said probe ions causing the fluorescent spectral bandwidth of said probe ions to broaden through the Doppler effect leading to a decline in the light absorption probability of said probe ions, said decline being detected in the form of a drop in fluorescence intensity, said drop in fluorescence intensity being interpreted as changes in the velocity distribution of said probe ions.

7. An ion trapping mass spectrometry method according to claim 2, wherein either changes in the fluorescence intensity of said probe ions or changes in the spatial distribution thereof are detected synchronously with the frequency of said analyzing AC electric field for resonating said sample ions.

8. An ion trapping mass spectrometry method according to claim 2, wherein said analyzing AC electric field for resonating said sample ions has a mixture of a plurality of frequencies, and wherein temporal changes in the detected fluorescence intensity are subjected to Fourier transformation for resolution into an intensity distribution of varying frequency components, said intensity distribution being interpreted to identify the mass-to-charge ratio and the stored quantity of said sample ions.

9. An ion trapping mass spectrometry method according to claim 2, wherein said probe ions are laser-cooled ions.

10. An ion trapping mass spectrometry method according to claim 2, wherein said probe ions are laser-cooled ions, and wherein said probe ions are cooled by said laser beam to form an ion crystal state comprising said sample ions, said ion crystal state being observed as an image for a lattice structure.

11. An ion trapping mass spectrometer comprising:
   (a) a plurality of ion trapping electrodes forming an ion trapping region in which to trap sample ions;
   (b) sample ion introducing means for introducing said sample ions into said ion trapping region;
   (c) probe ion introducing means for introducing into said ion trapping region probe ions of which the mass-to-charge ratio is known;
   (d) laser radiating means for radiating a laser beam having a predetermined wavelength to said probe ions;
   (e) AC voltage applying means for applying an AC voltage having a predetermined frequency to some of said ion trapping electrodes so as to cause an analyzing AC electric field to act on said sample ions; and
   (f) detecting means used when said sample ions oscillate depending on the mass-to-charge ratio thereof under the influence of said analyzing AC electric field, the oscillating sample ions interacting with said probe ions in a Coulomb collision leading to kinetic changes of said probe ions inside said ion trapping region, said detecting means detecting scattered fluorescence changes resulting from said kinetic changes of said probe ions.

12. An ion trapping mass spectrometer according to claim 11, wherein at least one of said plurality of ion trapping electrodes is made of either a metal rod having at least one through hole or a metal mesh, and wherein said detecting means for detecting scattered fluorescence changes is a photo detector for detecting the fluorescence of said probe ions, said fluorescence being guided to said photo detector via an optical waveguide disposed close to said through hole or said metal mesh.

13. An ion trapping mass spectrometer according to claim 11, wherein said AC voltage applying means for causing said analyzing AC electric field to act on said sample ions varies the frequency of said AC electric field over time.

14. An ion trapping mass spectrometer according to claim 11, further comprising adjusting means for adjusting a radiating position and a degree of focusing for radiating said laser beam to excite said probe ions.

15. An ion trapping mass spectrometer according to claim 11, wherein said AC voltage applying means for causing said analyzing AC electric field to act on said sample ion provides a mixture of a plurality of frequencies, and wherein said detecting means for detecting fluorescence temporal changes is capable of effecting Fourier transformation.

16. An ion trapping mass spectrometer according to claim 11, wherein said detecting means for detecting fluorescence changes from said probe ions is capable of fluorescence change detection synchronously with the frequency of said analyzing AC electric field for resonating said sample ions.

17. An ion trapping mass spectrometer comprising:
   (a) a plurality of ion trapping electrodes forming an ion trapping region in which to trap sample ions, said ion trapping electrodes arranged in an axially linear manner including a mass spectrometry part and end electrodes placed at both ends of said mass spectrometry part, said mass spectrometry part comprising quadruple electrode portions constituting a linear ion trapping structure, said end electrodes being composed of one or more electrodes with a means to supply DC bias to said end electrodes to confine both the probe and sample ions within the trap axially;
   (b) sample ion introducing means for introducing said sample ions into said ion trapping region;
   (c) probe ion introducing means for introducing into said ion trapping region probe ions of which the mass-to-charge ratio is known;
   (d) laser radiating means for radiating a laser beam having a predetermined wavelength to said probe ions;
   (e) AC voltage applying means for applying an AC voltage having a predetermined frequency to some of said ion trapping electrodes so as to cause an analyzing AC electric field to act on said sample ions; and
   (f) detecting means used when said sample ions oscillate depending on the mass-to-charge ratio thereof under the influence of said analyzing AC electric field, the oscillating sample ions interacting with said probe ions in a Coulomb collision leading to kinetic changes of said probe ions inside said ion trapping region, said detecting means detecting scattered fluorescence changes resulting from said kinetic changes of said probe ions.

18. An ion trapping mass spectrometer according to claim 17, wherein said AC voltage applying means for causing said analyzing AC electric field to act on said sample ions varies the frequency of said analyzing AC electric field over time.

19. An ion trapping mass spectrometer according to claim 17, further comprising adjusting means for adjusting a radiating position and a degree of focusing for radiating said laser beam to excite said probe ions.

20. An ion trapping mass spectrometer according to claim 17, wherein said AC voltage applying means for causing said analyzing AC electric field to act on said sample ions provides a mixture of a plurality of frequencies, and wherein said detecting means for detecting fluorescence temporal changes is capable of effecting Fourier transformation.

21. An ion trapping mass spectrometer according to claim 17, wherein said detecting means for detecting fluorescence changes from said probe ions is capable of fluorescence change detection synchronously with the frequency of said analyzing AC electric field for resonating said sample ions.

22. An ion trapping mass spectrometer according to claim 17, wherein said probe ions are laser-cooled ions, and wherein said laser radiating means radiates a laser beam having a wavelength such that said laser beam excites and cools said probe ions at the same time.

23. An ion trapping mass spectrometer according to claim 22, wherein said detecting means for detecting fluorescence changes is arranged to be observed in the form of a lattice image of an ion crystal state created inside said ion trapping region.

24. An ion trapping mass spectrometer according to claim 17, further comprising at least two mass spectrometry parts arranged in an axially linear manner, each mass spectrometry part including quadruple electrode portions constituting a linear ion trapping structure, one of said mass spectrometry parts being a quadruple electrode filter forming an ion trapping structure for removing specific background ions from the ions generated from a sample, one of said mass spectrometry parts being a linear ion trap for generating laser-cooled probe ions with a means to mix said laser-cooled ions with said sample ions.

* * * * *

UNITED STATES PATENT AND TRADEMARK OFFICE
CERTIFICATE OF CORRECTION

PATENT NO. : 5,679,950

DATED : 21 October 1997

INVENTOR(S) : Takashi BABA et al.

It is certified that error appears in the above-identified patent and that said Letters Patent is hereby corrected as shown below:

| Column | Line | |
|---|---|---|
| 2 | 1 | Change "D" to --$\Omega$--. |
| 2 | 2 | Change "$2r_o$" to --$2r_0$--. |
| 11 | 48 | After "high" insert --isotopic--. |
| 12 | 23 | Change "$6^2S_{1/2+ee}$" to --$6^2S_{1/2}$--; change "$6^2P_{+e,fra\ 1/2}$" to --$6^2P_{1/2}$--. |
| 12 | 25 | Change "$5^2D_{3/2+ee}$" to --$5^2D_{3/2}$--; change "$6^2P_{+e,fra\ 1/2}$" to --$6^2P_{1/2}$--. |
| 15 | 32 | Change "firs fly" to --firstly--. |
| 20 | 27 | Change "ram," to --mm,--. |

Signed and Sealed this

Fifth Day of May, 1998

Attest:

BRUCE LEHMAN

*Attesting Officer*      *Commissioner of Patents and Trademarks*